(12) United States Patent
Vaghefi Rezaei

(10) Patent No.: US 11,854,199 B2
(45) Date of Patent: *Dec. 26, 2023

(54) METHODS AND SYSTEMS FOR OCULAR IMAGING, DIAGNOSIS AND PROGNOSIS

(71) Applicant: Auckland UniServices Limited, Auckland (NZ)

(72) Inventor: Seyed Ehsan Vaghefi Rezaei, Auckland (NZ)

(73) Assignee: Auckland UniServices Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,928

(22) Filed: Dec. 14, 2022

(65) Prior Publication Data

US 2023/0120295 A1   Apr. 20, 2023

Related U.S. Application Data

(63) Continuation of application No. 17/250,845, filed as application No. PCT/NZ2019/050121 on Sep. 12, 2019.

(30) Foreign Application Priority Data

Sep. 12, 2018   (NZ) ........................................ 746320

(51) Int. Cl.
*G06T 7/00* (2017.01)
*G06T 7/33* (2017.01)

(52) U.S. Cl.
CPC .............. *G06T 7/0012* (2013.01); *G06T 7/33* (2017.01); *G06T 2207/10088* (2013.01);
(Continued)

(58) Field of Classification Search
CPC .................... G06T 7/0012; G06T 7/33; G06T 2207/10088; G06T 2207/10101;
(Continued)

(56) References Cited

U.S. PATENT DOCUMENTS 9,934,364 B1 * 4/2018 Kumar ................... G06N 3/045
10,468,142 B1 * 11/2019 Abou Shousha ...... G16H 30/20
(Continued)

FOREIGN PATENT DOCUMENTS

WO   WO 02/097714 A1   12/2002

OTHER PUBLICATIONS

Frangi, A.F et al. 1998 "Multiscale vessel enhancement filtering" In Medical Image Computing and Computer-Assisted Intervention—MICCAI'98, W.M. Wells, A. Colchester and S.L. Delp (Eds.), Lecture Notes in Computer Science, vol. 1496—Springer Verlag, Berlin, Germany, pp. 130-137.
(Continued)

*Primary Examiner* — Van D Huynh
(74) *Attorney, Agent, or Firm* — Knobbe, Martens, Olson & Bear, LLP

(57) ABSTRACT

Embodiments of the invention involve combining data representative of the eye obtained from multiple modalities into a virtual model of the eye. The multiple modalities indicate anatomical, physiological, and/or functional features of the eye. The data from different modalities is registered in order to combine the data into the virtual model. Further embodiments involve analysing eye data, for example in the form of the virtual model, using neural networks to obtain insights about medical conditions of the eye, for example the diagnosis or prognosis of conditions, and/or predicting how the eye will respond to certain treatments.

13 Claims, 31 Drawing Sheets

(52) U.S. Cl.
CPC ............... *G06T 2207/10101* (2013.01); *G06T 2207/10116* (2013.01); *G06T 2207/10132* (2013.01); *G06T 2207/20081* (2013.01); *G06T 2207/20084* (2013.01); *G06T 2207/30041* (2013.01)

(58) Field of Classification Search
CPC . G06T 2207/10116; G06T 2207/10132; G06T 2207/20081; G06T 2207/20084; G06T 2207/30041
USPC .......................................................... 382/128
See application file for complete search history.

(56) References Cited

U.S. PATENT DOCUMENTS

| | | | | |
|---|---|---|---|---|
| 2017/0156582 | A1* | 6/2017 | Ehlers | G16H 50/30 |
| 2018/0160894 | A1* | 6/2018 | Gupta | A61B 5/4842 |
| 2019/0206054 | A1* | 7/2019 | Mao | G06T 7/73 |
| 2021/0057103 | A1* | 2/2021 | Abou Shousha | G06N 3/045 |

OTHER PUBLICATIONS

International Search Report and Written Opinion in PCT/NZ2019/050121, dated Jan. 27, 2020.
Katuwal, Gajendra Jung, et al., "Automatic Fundus Image Field Detection and Quality Assessment," 2013 IEEE Western New York Image Processing Workshop (WNYIPW), Rochester, NY, USA, 2013, pp. 9-13, doi: 10.1109/WNYIPW.2013.6890980.
De Zanet, Sandro I., et al., "Landmark Detection for Fusion of fundus and MRI Toward a Patient-Specific Multimodal Eye Model," IEEE Transactions on Biomedical Engineering, vol. 62, No. 2, Feb. 2015.
Chen, Jian, et al., "A Partial Intensity Invariant Feature Descriptor for Multimodal Retinal Image Registration," IEEE Transactions on Biomedical Engineering, vol. 57, No. 7, Jul. 2010; 1707-1718.
Jiang, Jiewel, et al., "Predicting the progression of ophthalmic disease based on slit-lamp images using a deep temporal sequence network", PLoS One, Jul. 31, 2018.
Kumar, Ashnil, et al. "An ensemble of fine-tuned convolutional neural networks for medical image classification." *IEEE journal of biomedical and health informatics* 21.1 (2016): 31-40.
Vogl, Wolf-Dieter, et al., "Spatio-Temporal Signatures to Predict Retinal Disease Recurrence", Information Processing in Medical Imaging, Springer International Publishing, 2015.

* cited by examiner

METHODS AND SYSTEMS FOR OCULAR IMAGING, DIAGNOSIS AND PROGNOSIS

TECHNICAL FIELD

The invention generally relates to the field of ocular imaging. More particularly, the invention relates to image processing systems and methods for ocular diagnosis, treatment planning and prognosis.

BACKGROUND

Improving the accuracy and efficacy of ophthalmic imaging is a desirable goal to assist in the diagnosis and treatment of numerous diseases of the eye, including but not limited to macular degeneration, glaucoma, cataract and diabetic retinopathy. Ophthalmic imaging is employed for a number of applications relating to diseases of the eye, including predicting the likelihood of a disease, diagnosis, progression, treatment efficacy, or relapse. However, it can be difficult to effectively diagnose eye conditions in patients in a consistent and systematic manner using current imaging techniques which often suffer from limited resolution, limited field of view or poor contrast, detail or other clinically important data.

Furthermore, most ophthalmic interventions range from being highly effective to not at all effective in otherwise similar cohorts of patients. However, to date it is difficult for clinicians to pre-identify patients that will respond well to treatment from patients who will not respond well. Since the clinical treatment plan for these groups of patients may be markedly different, it is highly desirable to categorise individuals prior to intervention initiation.

The eye is subject to diseases such as age-related macular degeneration (AMD), glaucoma, diabetic retinopathy, and many others. In the case of AMD, this has two general forms: dry (non-proliferative) and wet (proliferative). Dry AMD is the initial prognosis of this disease, which will eventually lead to the wet form. About 80% of AMD sufferers have the dry form, which is not vision threatening, and the rest suffer from wet AMD. While AMD cannot be treated, its progression can be stopped or significantly slowed down using intravitreal anti vascular endothelial growth factor (anti-VEGF) injections. These injections are administrated by an ophthalmologist, approximately every 6-12 weeks. Currently, there are several hurdles in treatment of AMD. A major issue is the inter-patient variability of AMD progression and treatment response. The conversion timeframe of dry patients to the wet form varies greatly (from months to decades) in the public, the conversion criteria of dry patients (mild dry to very advanced) to the wet form varies greatly within the population, wet AMD progression rate (post-conversion) also varies greatly in different patients (from weeks to one year), and anti-VEGF treatments do not benefit all the patients to the same degree. In most cases, anti-VEGF injections are only needed every 6-12 weeks, with longer intervals after 3-4 years of treatment, however, some patients stop responding to these injections after a couple of years, and some AMD patients never respond to anti-VEGF injections. Also the intensity of monitoring and frequency of subsequent interventions depends on the how well patients respond to treatment. Some poor responders may be reclassified as non-responders and be referred on to other, sometimes more invasive, treatments such as laser therapy.

Currently available imagining and diagnostic tools for AMD and other eye diseases can result in missed diagnosis and the inability to predict who will respond to treatment, and how well.

OBJECT

It is an object of the invention to provide an improved method and/or system for ocular imaging and diagnosis. Alternatively, it is an object to provide an improved method and/or system for ocular diagnosis, prognosis and treatment that goes at least some way to addressing the aforementioned problems. Alternatively, it is an object to provide an improved method for generating data representative of a model of an eye. Alternatively, it is an object to provide an improved method for diagnosing disease in an eye. Alternatively, it is an object to provide an improved method for prognosing disease in an eye. Alternatively, it is an object of the invention to at least provide the public with a useful choice.

SUMMARY

Aspects of the present invention are directed towards image processing systems and methods for ocular diagnosis, prognosis and treatment. More particularly, aspects of the present invention are directed towards combining different types of ocular imaging data to generate a model of the eye which can be used for improved diagnosis, prognosis and treatment, and may also be used for other applications such as visualisation, surgeon training and robotic surgery. The different types of ocular imaging data may be obtained using different imaging systems, including but not limited to magnetic resonance imaging (MRI), optical coherence tomography (OCT), optical coherence tomography angiography (OCTA), ultrasound, keratometry, corneal topography imaging, laser speckle flowmetry and fundus photography.

According to one aspect there is provided a computer-implemented image processing method for an eye, the method comprising:
  processing first eye image data of the eye in order to generate first processed image data;
  processing second eye image data of the eye in order to generate second processed image data; and
  combining the first and second processed image data to generate an ocular model of the eye.

Processing the first and second eye image data may comprise one or more of the following: identifying anatomical features; enhancing clarity of anatomical features; and applying coordinate metadata to anatomical features, co-registering the anatomical features using common coordinate metadata.

In an embodiment, the first eye image data corresponds to a 3D image of at least part of the eye and the second eye image data corresponds to a 2D image of the same eye. In an embodiment, common landmarks of the 3D and 2D images are identified, one of the 3D and 2D images aligned and scaled to match the other, and the 2D image warped onto the 3D image to generate the ocular model. Landmarks may include blood vessels, macula, fovea, optic disk, retina, eye boundary, vitreous humour, aqueous humour, ciliary muscles, and lens.

In an embodiment, the first eye image data is derived from an image processing system, which captures static information such as anatomical details. Examples of such systems include fundus photography, magnetic resonance imaging (MRI), X-ray, computer tomography (CT), optical coherence tomography (OCT), ultrasound, and biometry. The second eye image data may be derived from an image processing system, which captures dynamic information or changes in the eye, such as physiological details. Examples of such systems include MRI (in different modes), optical coherence tomography angiography (OCTA), and retinal perfusion maps. In an embodiment, fundus photography is used to capture anatomical details of the retina, and OCTA is used to capture blood flow in the retina. Blood vessels may be identified from both data sets and the information combined to generate a better representation of these blood vessels in the ocular model. This may be advantageous as micro-vessels are clinically important for diagnosis, prognosis, and monitoring treatment efficacy.

In another embodiment, the first and second eye image data are determined from different imaging modalities. The different imaging modalities may include MRI, fundus photography, OCT, OCTA, laser speckle (LS) flowmetry and other imaging techniques. The different modalities may determine the same or different aspects of the eye, for example anatomical, physiological or functional features.

In an embodiment, the ocular model may be used for diagnosis, prognosis, monitoring of treatment efficacy, visualisation, surgical training, and robotic surgery.

In an embodiment the first eye image data is a 3D MRI image and the second eye image data is a 2D fundus photo image. Processing the second eye image data to generate second processed image data comprises identifying blood vessels. The identification of blood vessels may use a vesselness probability parameter. The process may also include removing short vessels having less than a threshold number of pixels. The remaining identified blood vessels may be skeletonised to generate a vessel mask. A green channel of the fundus image may be used for identifying the blood vessels. The vessels in the vessel mask may be classified as veins or arteries using the vessel hue and/or thickness.

In an embodiment the second eye image data may be further processed by thresholding the blue channel to identify pixels associated with the macula, and segmenting the macula by fitting a circle to the identified pixels. The fovea may be located as the centre of the fitted circle.

The first and second processed image data may be combined by identifying landmarks and using these to align the image data. For example, the line between the optic disc and fovea in the fundus image may be rotated to be parallel with a line between the optic disc and the optical size in the MRI image. One or both image data may be resized by determining a real-life distance between landmarks from a pixel distance using the resolution of the equipment used to generate the eye image data. One image may be translated to another using a common landmark such as the optic disc. The resized, rotated and translated 2D image may be warped onto a corresponding part of the 3D image to generate the ocular model.

In another embodiment the first eye image data is a 3D MRI image and the second eye image data is a 3D OCT, OCTA or LS image. Processing the second eye image data to generate second processed image data comprises flattening the 3D image to a 2D image. Identifying blood vessels in the flattened 2D image using a "vesselness" probability parameter. The process may also include removing short vessels having less than a threshold number of pixels. The remaining identified blood vessels may be skeletonised to generate a vessel mask. A green channel of the fundus image may be used for identifying the blood vessels. The vessels in the vessel mask may be classified as veins or arteries using the vessel hue and/or thickness.

For each vessel pixel in the flattened 2D image, the highest intensity pixel having the same 2D coordinates is located in the third dimension of the 3D image in order to generate a 3D vessel mask. The vessels of the 3D vessel mask may be dilated, and 3D skeletonised.

The third and second processed image data may be combined using the minimum absolute difference between the two vessel masks. In an embodiment, a flattened 2D representation of the third processed image data (eg OCT) is moved along the surface of the 3D representation of the second image data (eg warped fundus) and the absolute difference between the vessel masks of each is determined. The 2D representation of the third image data may be angled at each location. The best location (and angle) of the 2D representation of the third image data in comparison to the second image data has the lowest absolute difference. The best 2D representation of the third image data may then also be rotated, translated and resized using the lowest absolute difference of its vessel masks compared with the vessel masks of the second image data. The unflattened 3D representation of the third image data is then located on the third dimension of second image data. This may be done by aligning the mid-points of the edges of the third image data with the surface of the second image data.

The "vesselness" probability parameter may be calculated from:

$$V = \begin{cases} 0, \text{ if } \lambda_2 > 0 \\ \exp\left(-\frac{R_B^2}{2\beta^2}\right)\left(1 - \exp\left(-\frac{S^2}{2c^2}\right)\right), \end{cases}$$

Where $$R_B = \frac{\lambda_1}{\lambda_2} \text{ and } S = \sqrt{\lambda_1^2 + \lambda_2^2},$$

and $\lambda_1$, $\lambda_2$, are the Hessian and eigenvalue of the Hessian, where $|\lambda_1| < |\lambda_2|$, and $\beta$ and C are threshold parameters which can be determined and adjusted to control the sensitivity of the vesselness parameter.

In another aspect there is provided of computer-implemented image processing method for segmenting blood vessels for an eye, the method comprising:
  determining 2D image data of the blood vessels of the eye;
  identifying blood vessels within the 2D image data using a "vesselness" probability parameter;
  skeletonising the identified blood vessels to generate a 2D vessel mask.

Blood vessels may be identified by having a "vesselness" parameter above a threshold. The method may also include removing short vessels having less than a threshold number of pixels. A green channel of a fundus image may be used for identifying the blood vessels. The vessels in the vessel mask may be classified as veins or arteries using the vessel hue and/or thickness.

In another aspect there is provided a computer-implemented image processing method for segmenting blood vessels for an eye, the method comprising:
  flattening a 3D image of the eye;
  segmenting the blood vessels to generate a 2D vessel mask;

for each 2D location of a blood vessel, identifying a highest intensity pixel in the third dimension of the 3D image in order to generate a 3D vessel mask.

Segmenting the blood vessels may use a "vesselness" parameter. The vessels of the 3D vessel mask may be dilated, and 3D skeletonised.

In another aspect there is provided a computer-implemented image processing method for segmenting an eye, the method comprising:
determining 2D colour image data of the eye;
thresholding the blue channel to identify pixels associated with the macula;
segmenting the macula by fitting a circle to the identified pixels.

In an embodiment the fovea may be located as the centre of the fitted circle.

In another aspect there is provided a computer-implemented method of determining anisotropy of retinal perfusion, the method comprising:
determine images of perfusion in retinal layers;
generate a flattened enface image of perfusion in the retinal layers;
determine perfusion in the flattened image using a pixel intensity threshold;
determine the maximum pixel intensity in the un-flattened perfusion images in order to determine perfusion in a 3D image of the retinal layers;
calculate anisotropy maps from the 3D image.

The anisotropy calculation may be made using fractional anisotropy, relative anisotropy or volume ratio.

In an embodiment, shadow artefacts are removed by generating two flattened images of perfusion, the first image of a number of the outer layers of the retina and the second image of a number of inner layers of the retina. Blood vessels are identified in each image to generate respective vessel masks. The difference in vessel masks is used to identify shadow vessels or artefacts and these are removed from the step of determining perfusion. Low perfusion or dark areas may be determined using a pixel intensity threshold. The maximum pixel intensity in the un-flattened perfusion images of these dark areas may be determined in order to enhance the 3D image of the retinal layers.

In an embodiment the calculated anisotropy map is used to make a diagnosis or prognosis for the eye.

In another aspect there is provided a computer-implemented method of diagnosing disease in an eye, the method comprising:
generating anisotropy maps of retinal perfusion;
applying the anisotropy maps to a trained neural network in order to generate diagnostic or prognostic parameters for the eye.

In an embodiment the anisotropy maps are generated by determining images of perfusion in retinal layers; generating a flattened enface image of perfusion in the retinal layers; determining perfusion in the flattened image using a pixel intensity threshold; determining the maximum pixel intensity in the un-flattened perfusion images in order to determine perfusion in a 3D image of the retinal layers; and calculating the anisotropy maps from the 3D image.

According to another aspect there is provided a computer-implemented method for diagnosing disease in an eye, the method comprising:
determining a first type of data relating to the eye;
determining a second and different type of data relating to the eye;
using the first and second type of data to generate diagnostic or prognostic parameters for the eye.

The first and second data types may be one of more of: imaging data from different imaging modalities (eg MRI, OCT, fundus photography); anatomical, physiological and/or function data. In an embodiment the anatomical and/or image data from different imaging modalities may be derived from the above defined ocular model. The physiological data may be derived from the above defined anisotropy of retinal perfusion method.

In an embodiment, the first type of data relating to the eye is applied to a first trained neural network and the second type of data relating to the eye is applied to a second trained neural network. The outputs of the two neural networks are used to generate diagnostic or prognostic parameters for the eye.

In an embodiment, matrices of change in the different data types are generated using first and second data obtained at different times. These different data types may be derived from the ocular model and/or the anisotropy of retinal perfusion method. The matrices of change may be used to make a prognosis for the eye.

In an embodiment the anatomical data corresponds to one or more 2D and/or 3D image data related to the eye. Anatomical data is related to relatively static structures of the eye, for example the retina, vitreous humour, and ciliary muscles. This may be derived from an image processing system such as fundus photography, magnetic resonance imaging (MRI), X-ray, computer tomography (CT), and optical coherence tomography (OCT). The anatomical data may be derived from the ocular model of the first aspect, or directly from the first and second processed image data of the first aspect.

In an embodiment, the physiological data is related to dynamic processes in the eye such as blood flow, aqueous or vitreous humour fluid flow. An example of physiological data is anisotropy maps of retinal perfusion, corneal surface changes due to age-related surface hydration changes, retinal thickness\volume changes due to intraocular pressure changes.

In an embodiment, the functional data is related to performance of the eye, for example, reading test results, night vision test results, ocular lens shape and refractive index changes during accommodation, visual acuity measurements, contrast sensitivity measurements.

In an embodiment, the method further comprises identifying changes in the anatomical and/or functional data over a series of time intervals in order to create change matrices for each data type. The change matrices may be input into a second CNN to generate predicted change matrices for the anatomical, physiological and/or functional data. The change predicted matrices may be used to generate predicted anatomical, physiological and/or functional data for inputting into the first CNN to determine a prognosis.

According to another aspect there is provided a computer-implemented image processing method for generating data representative of a model of an eye, the method comprising:
receiving first eye image data representative of the eye, the first eye image data being obtained from a first imaging modality;
processing the first eye image data to generate first processed eye image data, wherein the first processed eye image data has identified therein one or more features of the eye;
receiving second eye image data representative of the eye, the second eye image data being obtained from a second imaging modality, wherein the second imaging modality is different from the first imaging modality;

processing the second eye image data to generate second processed eye image data, wherein the second processed eye image data has identified therein one or more features of the eye;

registering the first processed eye image data and the second processed eye image data; and combining the registered first and second processed eye image data to generate data representative of a model of the eye.

In some embodiments, the first and second imaging modalities indicate features of the eye that are selected from the group consisting of: anatomical; physiological; and functional features.

In some embodiments, the first and second imaging modalities are selected from the group consisting of: magnetic resonance imaging (MRI); fundus photography; optical coherence tomography (OCT); optical coherence tomography angiography (OCTA); X-ray; computer tomography (CT); biometry; ultrasound; keratometry; corneal topography imaging; retinal perfusion mapping and laser speckle flowmetry.

In some embodiments, the first and second imaging modalities indicate features of the eye that are selected from different members of the group consisting of: anatomical; physiological; and functional features.

In some embodiments, the first imaging modality indicates anatomical features of the eye and is selected from the group consisting of: magnetic resonance imaging (MRI); fundus photography; optical coherence tomography (OCT); X-ray; computer tomography (CT); biometry; and ultrasound; and the second imaging modality indicates physiological features of the eye and is selected from the group consisting of: magnetic resonance imaging (MRI); optical coherence tomography angiography (OCTA); and retinal perfusion mapping.

In some embodiments, the first imaging modality is fundus photography and the first eye image data is representative of anatomical features of the retina.

In some embodiments, processing the first eye image data to generate first processed eye image data comprises identifying blood vessels.

In some embodiments, the second imaging modality is optical coherence tomography angiography (OCTA) and the second eye image data is representative of the blood flow in the retina.

In some embodiments, the second imaging modality is magnetic resonance imaging (MRI).

In some embodiments, the first imaging modality is 3D magnetic resonance imaging (MRI) and the second imaging modality is 3D optical coherence tomography (OCT), optical coherence tomography angiography (OCTA) or laser speckle flowmetry.

In some embodiments, the step of processing the first eye image data and/or the step of processing the second eye image data comprise(s) one or more of the following: identifying one or more features of the eye in the respective eye image data; enhancing clarity of one or more features of the eye in the respective eye image data; isolating image data representative of one or more features of the eye; and applying coordinate metadata to one or more features of the eye in the respective eye image data.

In some embodiments, the step of registering the first processed eye image data and the second processed eye image data comprises registering the one or more features in the first processed eye image data and the respective one or more features in the second processed eye image data.

In some embodiments, the one or more features in the first and second processed eye image data are any one or more features selected from the group consisting of: blood vessels; macula; fovea; optic disk; retina; eye boundary; vitreous humour; aqueous humour; ciliary muscles; and lens.

In some embodiments, the first processed eye image data is representative of a first eye image and the second processed eye image data is representative of a second eye image, and wherein the step of registering the first processed eye image data and the second processed eye image data comprises manipulating the first processed eye image data and/or the second processed eye image data to achieve any one or more of: translational alignment of the first and second eye images; rotational alignment of the first and second eye images; common scaling of the first and second eye images; flattening data representative of a 3D image into data representative of a 2D image.

In some embodiments, the method comprises:

receiving third eye image data representative of the eye, the third eye image data being obtained from a third imaging modality, wherein the third imaging modality is different from the first and second imaging modalities;

processing the third eye image data to generate third processed eye image data, wherein the third processed eye image data has identified therein one or more features of the eye;

registering the third processed eye image data and the first and second processed eye image data; and combining the registered first, second and third processed eye image data to generate data representative of the model of the eye.

In some embodiments, the method further comprises outputting the data representative of the model of the eye.

In some embodiments, the step of outputting the data representative of the model of the eye comprises displaying the model of the eye on a display device.

In some embodiments, the first eye image data is representative of a 3D image of at least part of the eye and the second eye image data is representative of a 2D image of the eye.

According to another aspect there is provided a computer-implemented method for diagnosing disease in an eye, the method comprising:

receiving first eye image data representative of the eye, the first eye image data being obtained from a first imaging modality;

receiving second eye image data representative of the eye, the second eye image data being obtained from a second imaging modality, wherein the second imaging modality is different from the first imaging modality;

analysing the first and second eye image data using an ensemble neural network to generate a diagnostic parameter for the eye, wherein the ensemble neural network comprises a first neural network to analyse the first eye image data and a second neural network to analyse the second eye image data, wherein the ensemble neural network comprises a fully connected layer receiving outputs from each of the first and second neural networks, the diagnostic parameter for the eye being output from the fully connected layer.

In some embodiments, the first and second imaging modalities indicate features of the eye that are selected from the group consisting of: anatomical; physiological; and functional features.

In some embodiments, the first and second imaging modalities are selected from the group consisting of: magnetic resonance imaging (MRI); fundus photography; optical coherence tomography (OCT); optical coherence tomography angiography (OCTA); X-ray; computer tomography (CT); biometry; ultrasound; keratometry; corneal topography imaging; retinal perfusion mapping and laser speckle flowmetry.

In some embodiments, the first and second imaging modalities indicate features of the eye that are selected from different members of the group consisting of: anatomical; physiological; and functional features.

In some embodiments, the method comprises receiving the first eye image data and the second eye image data as a combined data set.

In some embodiments, the method comprises receiving the first eye image data and the second eye image data in the form of data representative of a model of the eye.

In some embodiments, the data representative of the model of the eye is generated using the method of any one of the previous aspects of the invention.

In some embodiments, the method comprises weighting the outputs from each of the first and second neural networks in the fully connected layer.

In some embodiments, the method comprises:
generating first and second feature maps using each of the first and second neural networks respectively;
generating first and second one dimensional arrays from each of the first and second feature maps respectively; and
combining the first and second one dimensional arrays in the fully connected layer with a weighting.

In some embodiments, the method further comprises outputting the diagnostic parameter for the eye.

According to another aspect there is provided a computer-implemented method for prognosing disease in an eye, the method comprising:
receiving present eye image data representative of the eye at a present time;
analysing the present eye image data using a neural network to generate a prediction for future eye image data representative of the eye at a future time; and
generating a prognostic parameter for the eye from the future eye image data,
wherein the neural network is trained using past eye image data representative of a plurality of eyes at first and second past times to generate one or more eye image data change functions, wherein the eye image data change function is applied by the neural network to the present eye image data to generate the prediction for the future eye image data.

In some embodiments, the neural network is further trained using past eye image data representative of a plurality of eyes at a third past time to refine the eye image data change function.

In some embodiments, the past eye image data is first past eye image data and the present eye image data is first present eye image data, and the first past eye image data and the first present eye image data are obtained from a first imaging modality, and the method further comprises:
receiving second present eye image data representative of the eye at the present time, the second present eye image data being obtained from a second imaging modality, wherein the second imaging modality is different from the first imaging modality;
analysing the first and second present eye image data using the neural network to generate the prediction for future eye image data representative of the eye at the future time,
wherein the neural network is further trained using second past eye image data representative of the plurality of eyes at first and second past times in the second imaging modality to generate the eye image data change function.

In some embodiments, the first and second imaging modalities indicate features of the eye that are selected from the group consisting of: anatomical; physiological; and functional features.

In some embodiments, the first and second imaging modalities are selected from the group consisting of: magnetic resonance imaging (MRI); fundus photography; optical coherence tomography (OCT); optical coherence tomography angiography (OCTA); X-ray; computer tomography (CT); biometry; ultrasound; keratometry; corneal topography imaging; retinal perfusion mapping and laser speckle flowmetry.

In some embodiments, the first and second imaging modalities indicate features of the eye that are selected from different members of the group consisting of: anatomical; physiological; and functional features.

In some embodiments, the eye image data change function comprises one or more matrices of change.

In some embodiments, the neural network comprises a long short-term memory (LTSM) network.

In some embodiments, the neural network is an ensemble neural network comprising a first neural network to analyse past and/or present eye image data from the first imaging modality and a second neural network to analyse past and/or present eye image data from the second imaging modality, wherein the ensemble neural network comprises a fully connected layer receiving outputs from each of the first and second neural networks, the output of the fully connected layer being input to the long short-term memory (LTSM) network.

In some embodiments, the method comprises receiving the first past and/or present eye image data and the second past and/or present eye image data as a combined data set.

In some embodiments, the method comprises receiving the first past and/or present eye image data and the second past and/or present eye image data in the form of data representative of a model of the eye.

In some embodiments, the data representative of the model of the eye is generated using the method of any one of the previous aspects of the invention.

In some embodiments, the neural network is trained using past eye treatment data representative of prior treatments undergone by the plurality of eyes, and the method comprises generating a treatment prediction parameter comprising the prognostic parameter for the eye on the assumption a treatment is used on the eye.

In some embodiments, the method further comprises outputting the prognostic parameter for the eye.

According to another aspect there is provided a computer-implemented method for diagnosing disease in an eye, the method comprising:
receiving an anisotropy map of retinal perfusion for the eye; and
analysing the anisotropy map using a neural network to generate a diagnostic parameter for the eye.

In some embodiments, the method further comprises:
receiving a retinal perfusion map of retinal layers;
generating a flattened enface image of perfusion in the retinal layers;
determining perfusion in the flattened image using a pixel intensity threshold;
determining the maximum pixel intensity in the unflattened perfusion images in order to determine perfusion in a 3D image of the retinal layers; and
calculating the anisotropy map from the 3D image.

In some embodiments, the method further comprises calculating the anisotropy map using any one or more of the group consisting of: fractional anisotropy, relative anisotropy and volume ratio.

In some embodiments, the method further comprises outputting the diagnostic parameter for the eye.

According to another aspect of the invention there is provided a processor configured to implement a computer-implemented method according to any one of the previous aspects of the invention.

According to another aspect of the invention there is provided a system configured to implement a computer-implemented method according to any one of the previous aspects of the invention.

The above described methods may be combined either fully or partially with each other. A computer programmable device may be suitably programmed to carry out these methods. The device may be part of an image processing and/or diagnostic and/or prognostic system. The steps of the methods may be implemented as executable steps in a computer program transported or stored on a computer readable medium.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

Embodiments of the present invention are directed towards imaging the eye as well as diagnosis, treatment planning and prognosis in respect of diseases of the eye. In general terms some embodiments of the invention involve combining data representative of the eye obtained from multiple modalities into a virtual model of the eye. Further embodiments involve using that virtual model to obtain insights about medical conditions of the eye, for example the diagnosis or prognosis of conditions, and/or predicting how the eye will respond to certain treatments.

Figure 1:
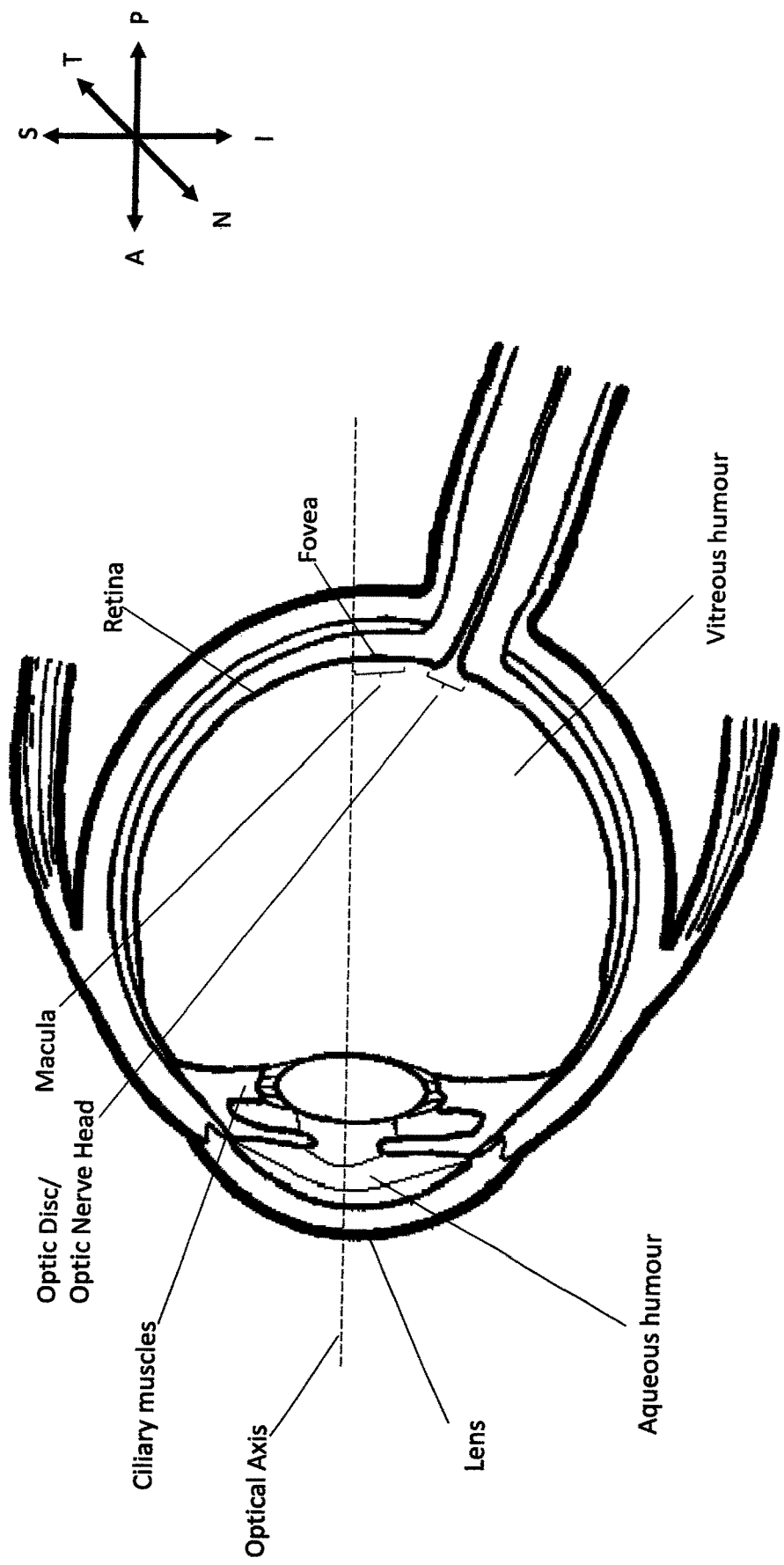
FIG. 1 is a cross-sectional schematic illustration of an eye indicating anatomical terms of the eye.

FIG. 1 is a cross-sectional schematic illustration of an eye indicating anatomical terms of the eye as referred to in this specification. A 3D coordinate system is also shown. The nasal/temporal (NT) axis is from left-to-right of the eye (into and out of the page in the figure), the inferior/superior (IS) axis is top to bottom of the eye (and also in the figure), and the anterior/posterior (AP) axis is front to back of the eye (left-to-right in the figure).

MRI Image Process

Figure 2A:
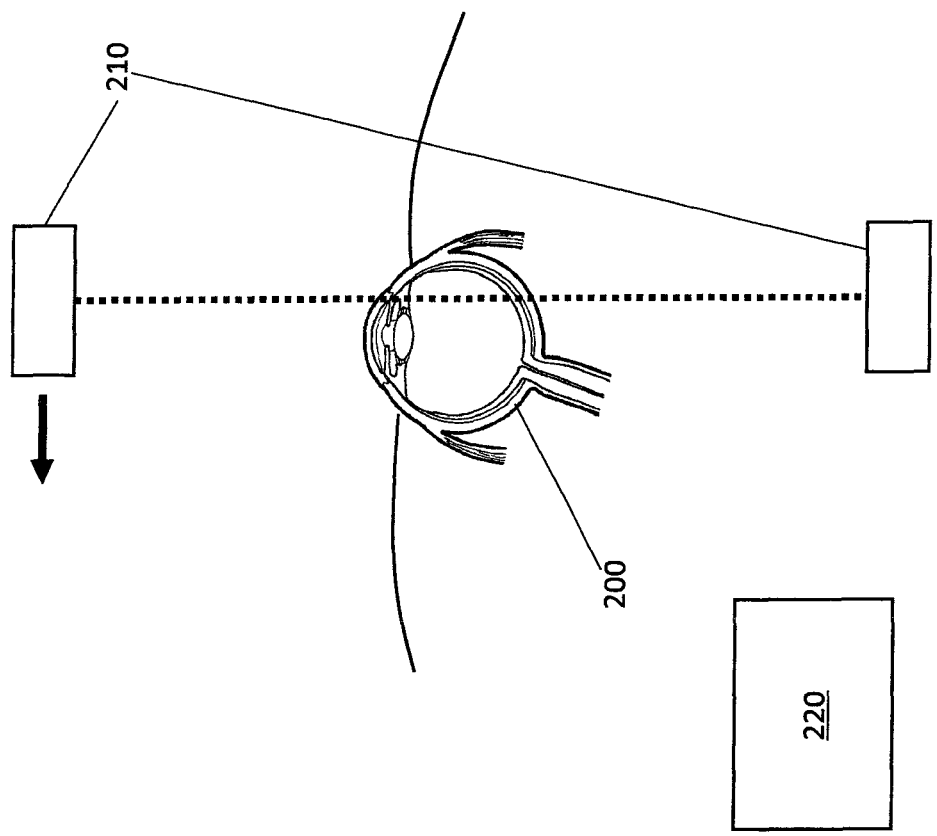
FIG. 2A illustrates an MRI scan of an eye.

FIG. 2A illustrates a magnetic resonance imaging (MRI) scan of an eye 200. An MRI scanner (not shown) applies a magnetic field to a narrow region of the body resulting in radio frequency (RF) emissions of excited water molecule atoms. These RF signals are detected by receiving coils and used to generate a narrow 3D image of the region. The same process is applied sequentially to adjacent regions of the body and the images pieced together to form a 3D image of the whole scanned region. In the figure, receiving coils 210 of an MRI scanner system are shown moving in a scanning direction indicated by the arrow. At each scanning location an imaging slice of the eye 200 is obtained, and these images pieced together to form a 3D image of the region. Isolation of the image data relating to the eye from image data relating to other surrounding parts of the body and identification of landmarks and other features is performed by a processing system 220. The resulting 3D MRI generated eye image corresponds to a first ocular image generated from a first imaging process, in this embodiment an MRI scan.

Fundus Photography Image Process

Figure 2B:
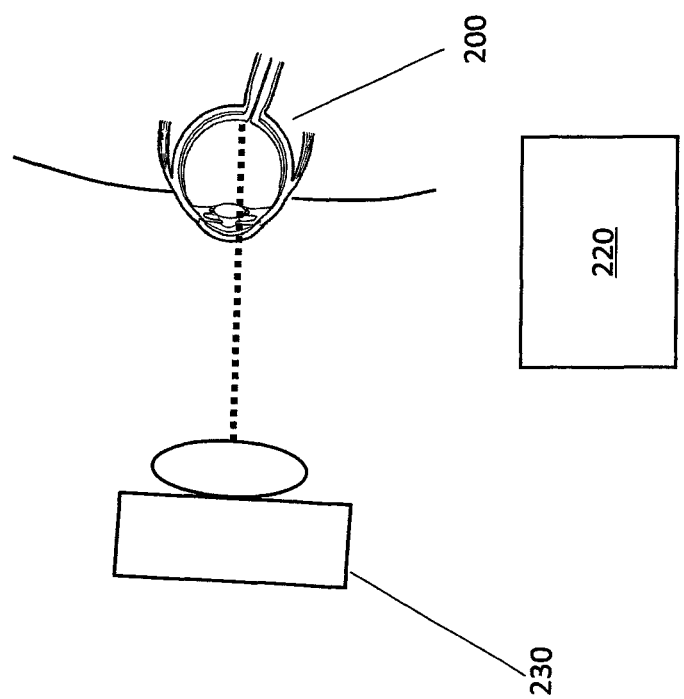
FIG. 2B illustrates fundus photography of an eye.

FIG. 2B illustrates fundus photography of the same eye 200 using a fundus camera 230. A fundus camera typically comprises an image capturing device held close to the exterior of the eye and which illuminates and photographs the retina to provide a 2D image of part of the interior of the eye 200. Many clinically important regions of the eye may be imaged, including the retina, macula, fovea, and optic disc. Identification of landmarks and other features of any one or more of these regions is performed by the processing system 220. The resulting 2D fundus image corresponds to a second ocular image generated from a second imaging process, in this embodiment a fundus camera.

Whilst MRI and fundus camera imaging are described in this embodiment, other types of imaging processing may additionally or alternatively be used. Examples include OCT (optical coherence tomography), MRA (magnetic resonance angiography), OCT Angiography, LS (laser speckle flowmetry), Fluorescein angiography (FA) or Indocyanine Green (ICG) angiography, ultrasound, biometry, keratometry, corneal topography imaging, laser speckle flowmetry, photography and refractometry. These different types or modalities of imaging processes capture different types of data, including anatomical, physiological and functional data, which may relate to relatively static features or changes indicative of biological processes. These images may be 2D, 3D, static, dynamic, colour, black and white, details of parts of the eye, and/or lower resolution information about the entire eye.

The combination of these different types or modalities of imaging data into a single ocular model can provide more accurate and/or more comprehensive information about the eye 200 compared to the information that is provided by, or can be discerned from, any of the types/modalities on their own. This ocular model may then be used in a number of applications including: visualisation or display of the eye; diagnosis of disease or abnormalities; prognosis; tracking or prediction of disease progression or treatment efficacy; surgeon training; and robotic surgery.

Processing System

Figure 3:
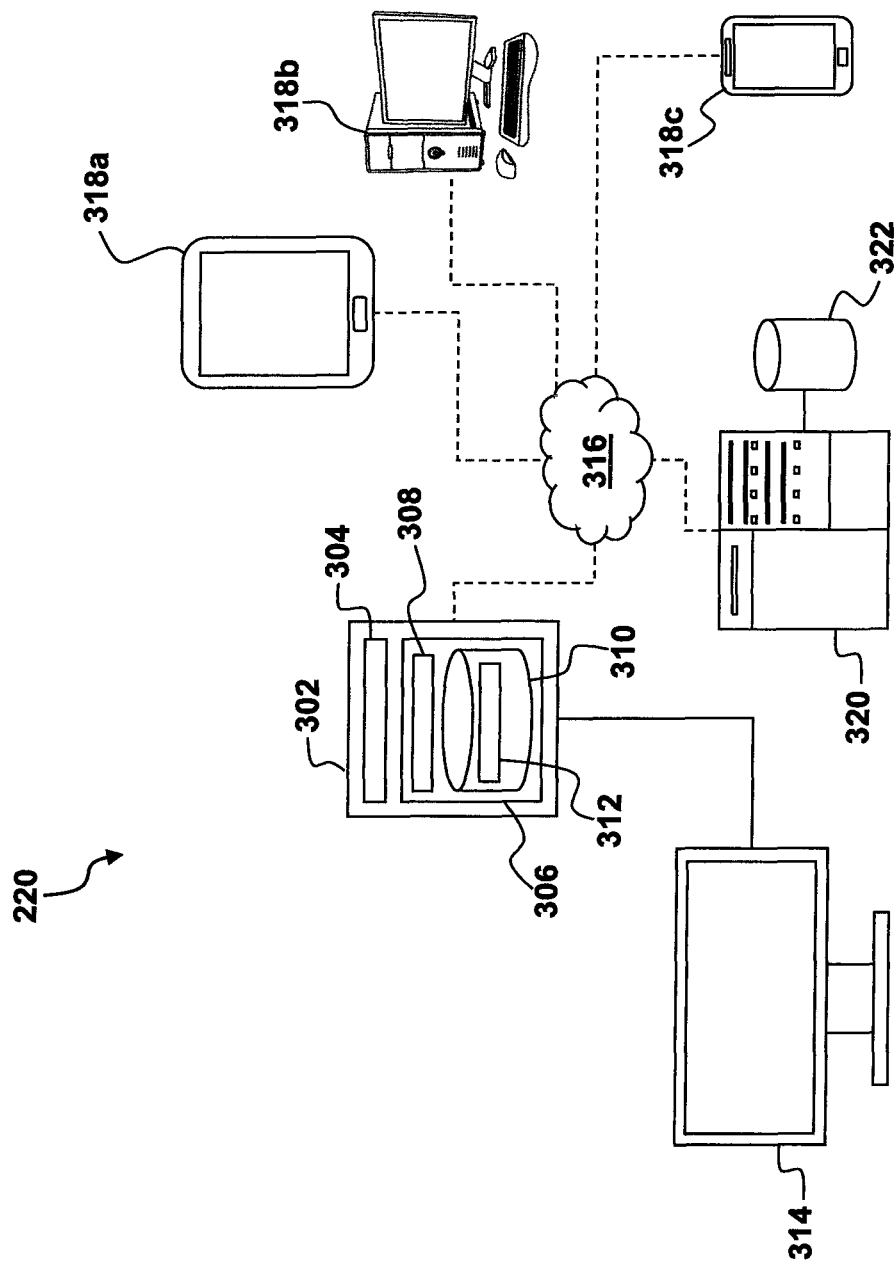
FIG. 3 is a schematic illustration of a processing system for use with an embodiment of the invention.

The processing system 220 according to an embodiment is shown in more detail in FIG. 3. Processing system 220 comprises a local hardware platform 302 that manages the collection and processing of data from the imaging processing systems 210, 230. The hardware platform 302 has a processor 304, memory 306, and other components typically present in such computing devices. In the exemplary embodiment illustrated the memory 306 stores information accessible by processor 304, the information including instructions 308 that may be executed by the processor 304 and data 310 that may be retrieved, manipulated or stored by the processor 304. The memory 306 may be of any suitable means known in the art, capable of storing information in a manner accessible by the processor 304, including a computer-readable medium, or other medium that stores data that may be read with the aid of an electronic device.

The processor 304 may be any suitable device known to a person skilled in the art. Although the processor 304 and memory 306 are illustrated as being within a single unit, it should be appreciated that this is not intended to be limiting, and that the functionality of each as herein described may be performed by multiple processors and memories, that may or may not be remote from each other or from the processing system 200. The instructions 308 may include any set of instructions suitable for execution by the processor 304. For example, the instructions 308 may be stored as computer code on the computer-readable medium. The instructions may be stored in any suitable computer language or format. Data 310 may be retrieved, stored or modified by processor 304 in accordance with the instructions 310. The data 310 may also be formatted in any suitable computer readable format. Again, while the data is illustrated as being contained at a single location, it should be appreciated that this is not intended to be limiting—the data may be stored in multiple memories or locations. The data 310 may also include a record 312 of control routines for aspects of the system 220.

The hardware platform 302 may communicate with a display device 314 to display the results of processing of the data. The hardware platform 302 may communicate over a network 316 with user devices (for example, a tablet computer 318a, a personal computer 318b, or a smartphone 318c), or one or more server devices 320 having associated memory 322 for the storage and processing of data collected by the local hardware platform 302. For example, applications such as diagnosis, prognosis, surgeon training and robotic surgery may be carried out by separate systems which receive ocular model data from the processing system 220. It should be appreciated that the server 320 and memory 322 may take any suitable form known in the art, for example a "cloud-based" distributed server architecture. The network 316 may comprise various configurations and protocols including the Internet, intranets, virtual private networks, wide area networks, local networks, private networks using communication protocols proprietary to one or more companies, whether wired or wireless, or a combination thereof.

Processing of MRI Images (First Ocular Image)

In the following description, various known and new image processing techniques are applied to the image data. For efficiency of explanation, the known techniques are implemented by computer implemented functions using the commercially available MATLAB software from Mathworks™ available at www.mathworks.com. However alternative software packages or other techniques may be used. For the sake of clarity, it is noted that these comments apply to all descriptions of processing techniques applied to the image data in this specification, not just those in this section.

The following description refers to the manipulation of images, for example drawing shapes on images, altering the intensity of pixels in an image, and selecting or limiting to a particular colour component of any image. In some embodiments of the invention, the processor 304 is configured to manipulate the visual representation of images in the described manner, for example outputting on a display a representation of an image with a shape superimposed upon it. However, it should be appreciated that, in other embodiments, the processor 304 is configured to analyse data representative of an image in a manner that is analogous to the respective manipulation of the visual representation of that image. For example, the processor 304 may, from the data representative of an image, determine the properties of a line that could be drawn on the visual representation of that image if the visual representation were to be generated, and to generate data indicative of such a line, without actually generating a visual representation of the image or the line on a display device. The ensuing description, while using language that is suggestive of the former situation (i.e. manipulation of visual representation of images), should not be construed in a way that is limited as such but to also cover the latter situation, where the analysis is performed at the level of the data and not at the level of the visual representation of the data. For the sake of clarity, it is noted that these comments apply to all descriptions of manipulating images in this specification, not just those in this section.

Figure 4:
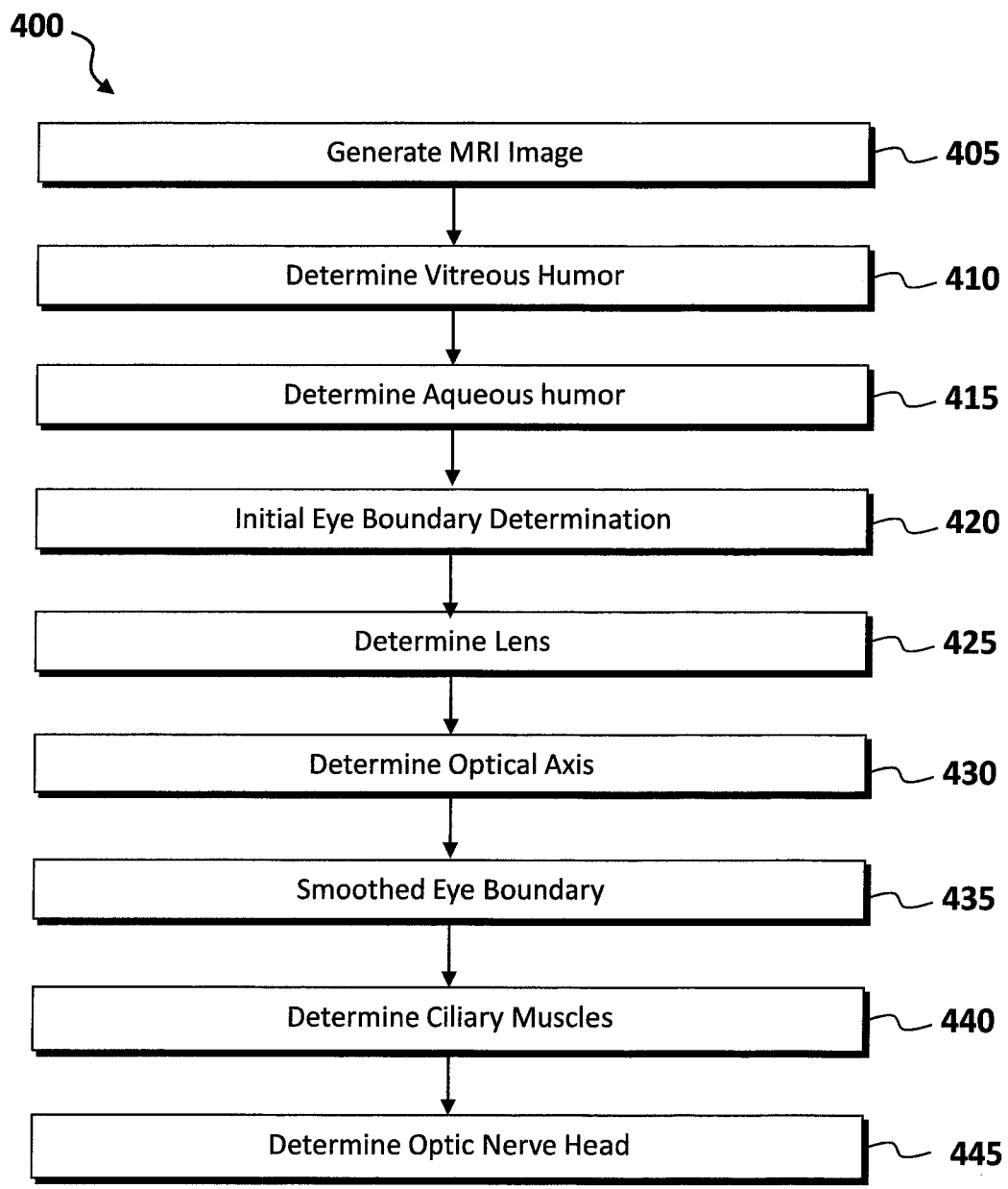
FIG. 4 is a flow chart of a method of processing MRI eye image data to generate MRI processed image data according to one embodiment of the invention.

A method of processing first or MRI eye image data to generate first or MRI processed eye image data according to an embodiment is shown in FIG. 4. The steps of this method (400) are described in more detail below and may be implemented using the processing system 220 of FIG. 3. The MRI image data may be read from an MRI dicom file and includes pixel intensity of the images (405). A Cartesian coordinate system is introduced, where the x-axis lies from left side to right side of the eye, the y-axis lies from anterior to posterior of the eye, and the z-axis spans from inferior to superior of the eye. These techniques can be implemented using known MATLAB functionality. An image slice where features of the eye can be clearly seen (usually the slice that goes through the middle of the eye) is selected and labelled as a mid-slice. The mid-slice is cropped to retain a region of interest using imcrop. The region of interest may include a boundary of the eye and the optic nerve. Crop properties, including the minimum x-coordinate, minimum y-coordinate, length and height of the cropped region, are stored.

The mid-slice is used to identify whether the images relate to the left or right eye. If the minimum x-coordinate of the cropped region is less than half the size of the mid-slice in the x-axis, this indicates the left eye and vice-versa.

The mid-slice is rotated so that the equator of the lens aligns with the x-axis. To do so, a threshold is set to identify the boundary of lens. The coordinates at the leftmost and rightmost edge of the lens are joined with a line. The angle between the line and the x-axis ($\theta_{rot}$) is used to rotate the cropped image using imrotate.

The first and last image slice where the eye can be observed are identified using known MATLAB functionality. These image slices are cropped using the same cropping properties applied for the mid-slice, followed by image rotation by $\theta_{rot}$. These processed images are used to extract point clouds for the boundary of the eye, the lens, the ciliary muscles, and the optic nerve attachment point, as described below. The term "point clouds" here refers to pixel intensity values and locations within a coordinate system and which correspond to surfaces of features—this can be thought of as both points in an image space for processing as well as the corresponding data stored in an appropriate file type.

On the MRI images, the boundary of an eye may be defined by the anterior boundary of the aqueous humour and the posterior boundary of the vitreous humour.

Determine Vitreous Humour (410):

To determine the vitreous humour, all processed image slices are thresholded so that pixels within the eye are labelled as 0 while background pixels are labelled as 1. The vitreous humour on each thresholded image is initially fitted with a circle using known image processing techniques from commercially available software such as Mathworks from MATLAB. These functions may return multiple fits but only fits that are completely within the boundary of the cropped image are retained. The fit with a centre closest to the top of the image may be selected as the best fit.

Figure 5A:
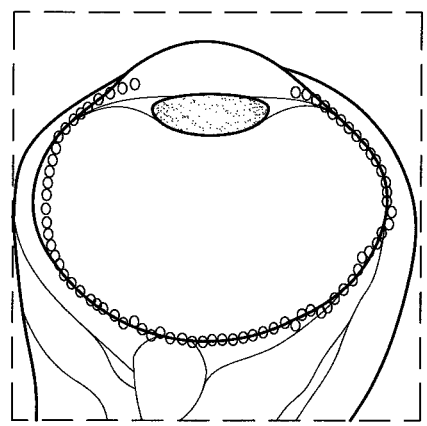
FIG. 5A-C illustrate boundary estimation of the vitreous humour, aqueous humour and improved aqueous humour according to one embodiment of the invention.

The vitreous humour region is made up of light pixels surrounded by a boundary of dark pixels. To estimate this dark boundary, a line is drawn from the centre of the fit to the bottom edge of the image. With the original cropped image (not thresholded), improfile may be applied over the line and the location of the pixel where a sharp decrease in pixel intensity first occurs may be recorded. The same line may be then incrementally rotated about the centre of the fit until the line has swept through all boundaries of the vitreous humour. At each angle increment, the line identifies the point where intensity decreases sharply. For each image, the x and y-coordinates of these pixel locations provide an estimate of the boundary of the vitreous humour (FIG. 5A).

Since the order of the image slices is known, z-coordinates are assigned to these data points depending on the image slice number. This results in a group of 3D data points which estimate the boundary surface of the vitreous humour based on MRI imaging. This set of 3D data points is then fitted to an ellipsoid using the linear least squares method using ellipsoid fit Determine Aqueous Humour (415):

Like the vitreous humour, the aqueous humour is also fitted as a circle with imfindcircles using the thresholded image. Only slices where the aqueous humour can be observed returns fits. In the case of multiple fits, the fitted circle with a centre above and closest to the centre of the fitted vitreous humour is chosen.

Figure 5B:
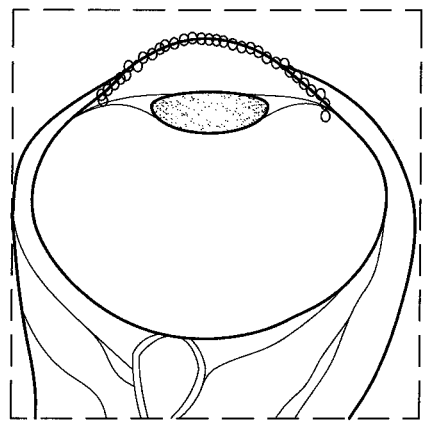

To estimate the boundary of the aqueous humour, a similar method as applied for the vitreous humour boundary estimation is used. Here, a line is plotted from the centre of the fitted aqueous humour circle to the top edge of the image. Improfile is implemented across the line on the original cropped image from outside the fitted circle to the centre. Since the background is made up of dark pixels, and the aqueous humour is made up of light pixels, transition across the aqueous humour boundary is given by a sharp increase in pixel intensity. Hence, the location of the first instance of sharp increase in pixel intensity is recorded. The line is incrementally rotated about the centre of the fitted aqueous humour circle until the line sweeps through the aqueous humour boundary, and the estimated locations of aqueous humour boundary is recorded (FIG. 5B).

By assigning z-coordinates to these points, a 3D point cloud which estimates the boundary surface of the aqueous humour is generated. Ellipsoid fitting of the point cloud gives rise to a 3D fitted surface which approximates the aqueous humour.

Figure 5C:
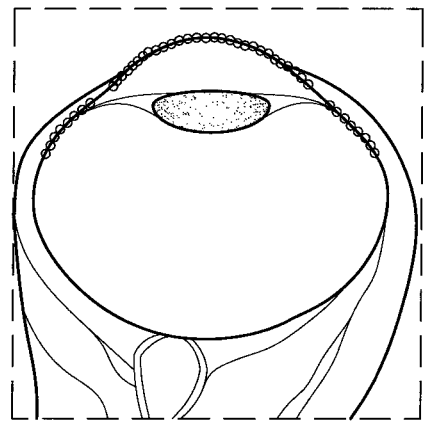

Initial Determination of Eye Boundary (420):

Direct combination of the fitted surfaces for the vitreous humour and aqueous humour gives rise to sharp boundaries at points where the surfaces intersect, which does not reflect the geometry of the eye. To overcome this issue, a new set of data points which better captures the curvature of the aqueous humour is consolidated for a second round of surface fitting. Image slices that contain both aqueous humour and vitreous humour are identified. The 3D ellipsoid fits for the vitreous humour and aqueous humour are used to work out the 2D fits to the vitreous and aqueous humours on the cross-sections of these slices. For each of these slices, the intersection points between the boundaries is determined using meetpoint. At each intersection point, a number (around 8) of data points from the vitreous humour 2D fit is appended to each end of the aqueous humour 2D fit to create a new set of data points for aqueous humour surface fitting (FIG. 5C). Ellipsoid fitting for aqueous humour is performed again on this new set of data points.

To combine the ellipsoidal fits for the vitreous and aqueous humour, the superior end of the eye is used as the starting point and traversed towards the inferior end. At each transverse plane, the ellipsoidal fits are used to work out the boundary of the vitreous and aqueous humour on the 2D cross-sectional plane. Intersection points between the two boundaries are determined using meetpoint and a complete boundary of the eye in that planar cross-section is formed by joining the fits for vitreous humour and aqueous humours at the intersection points. By compiling the data points on the boundary for all cross-sections, a fitted point cloud for boundary of the eye is obtained.

Determine Lens (425):

To determine the lens, from the mid-slice, a point lying between the leftmost and rightmost edges of the lens is assigned as $(x_{lens}, y_{lens})$. For every image slice with a lens, a line of a length that extends beyond the boundary of the lens is plotted from $(x_{lens}, y_{lens})$ towards the bottom edge of the image. Since the lens is made up of dark pixels, an increase in pixel intensity beyond a threshold value signifies transition out of the lens boundary. MATLAB function improfile is applied on the image along the line to identify the first instance on the line where pixel intensity exceeds a threshold value. The line is then incrementally rotated about $(x_{lens}, y_{lens})$ so as to identify the coordinates that approximate the lens boundary.

Figure 6A:
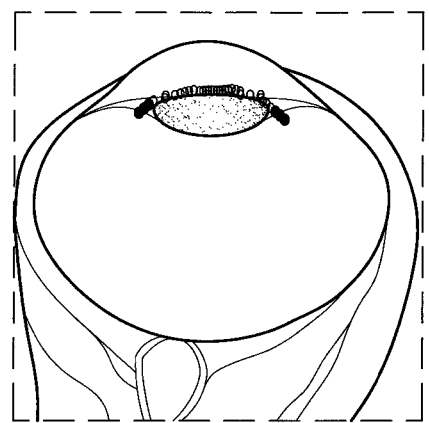
FIGS. 6A-B illustrate estimation of the anterior and posterior boundary of the lens according to one embodiment of the invention.
Figure 6B:
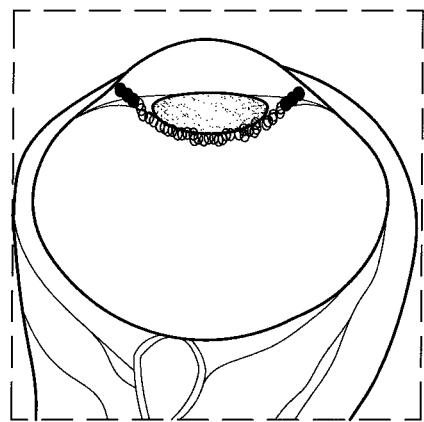

As the radius of curvature is usually different on the posterior and anterior sides of the lens, both surfaces are fitted separately. First, data points lying above the line joining the leftmost and rightmost edge of the lens are grouped as the anterior lens group, while points lying below the line fall into the posterior lens group. The anterior lens group is appended with a short tail on both ends such that the tails are pointing diagonally away in the posterior direction from the leftmost and rightmost points (see solid circles in FIG. 6A). For the posterior lens group, the same tail is appended to both ends but the tails point diagonally away in the anterior direction (see solid circles in FIG. 6B).

After the data points are obtained from all image slices containing a lens, z-coordinates are assigned to all the data points as previously described. Surface fitting is then performed on both posterior and anterior lens groups. Fitted surfaces for posterior and anterior lenses are combined by stepping through the transverse plane of the lens from superior to inferior. At each plane, the fitted surface is used to work out the anterior and posterior boundary of the lens in the 2D cross-section. The intersection point between the anterior and posterior lens boundary is found using meetpoint and the intersection points are used to join up the two boundaries. Data points lying on the boundary of the lens are compiled over the different cross-sections to create a fitted point cloud for the lens.

Determine Optical Axis (430):

The optical axis passes through the centre of the coronal plane of the lens. To obtain the optical axis, three lines between the most (1) anterior and posterior point, (2) inferior and superior point, and (3) nasal and temporal point of the lens are drawn. The intersection between all three lines provides the mid-point of the lens. An optical axis is created by plotting a line from the most anterior point to the most posterior point of the lens through the mid-point of the lens.

Determine Smoothed Eye Boundary (435):

Smoothing is carried out to remove asymmetry in the point cloud. A cylindrical coordinate system is introduced, and the optical axis which acts as an axis of reference is set as the z-axis in the cylindrical coordinate system. (Note that the z-axis in the cylindrical coordinate system does not correspond to the z-axis in the previously introduced Cartesian coordinate system.) The midpoint of the lens is set as the origin in the cylindrical coordinate system. Data points in all point clouds are converted from the original Cartesian coordinate system to the new cylindrical system.

Figure 7:
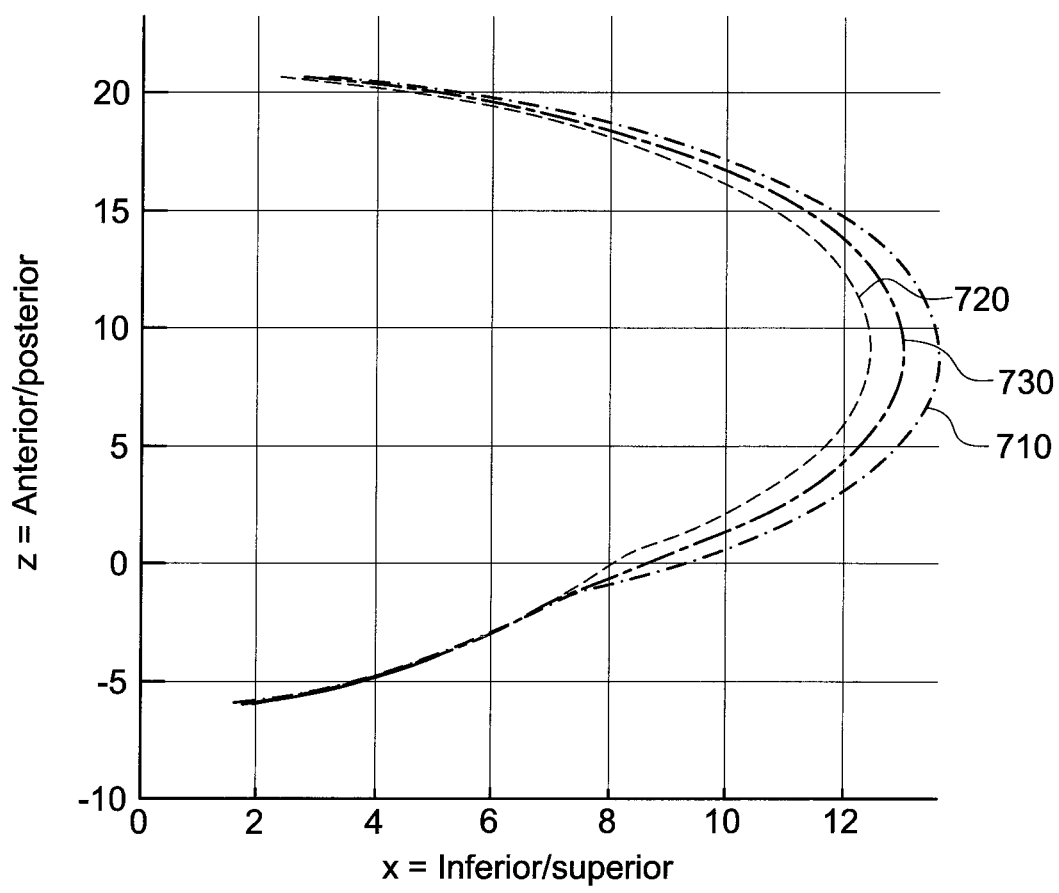
FIG. 7 illustrates smoothing of the boundary of the eye in the MRI processed image data according to one embodiment of the invention.

Using cylindrical coordinates, data points with azimuth close to a sampled angle are extracted from the point cloud for the eye boundary. As these points are unlikely to be evenly spread apart along the z-axis, interpolation (interp1) is applied to these points to create a first list of points that sit equally spaced apart along the z-axis and go through the original data points (line 710 in FIG. 7). The same steps are performed to create a second list of interpolated points from data points in the opposite quadrant (with azimuth of sampled angle+180°). The second set of interpolated points is reflected to lie on the same plane as the first set of points (line 720 in FIG. 7). At each z, the points from the first and second set are averaged. This results in a smoothed set of data points lying on the plane defined by the sample angle (line 730 in FIG. 7. The averaged points are reflected back to the sample angle+180° to attain geometric symmetry. The same steps are performed over a range of sample angles (e.g., every 10°) to attain overall smoothing of the data. Smoothing is performed on both the point cloud for the boundary of the eye as well as the lens.

Determine Ciliary Muscles (440):

To determine the ciliary muscles, thresholding is applied to the mid-slice so that pixels in the lens, the boundary of the aqueous humour, and the ciliary muscles are assigned as 1 while pixels in the aqueous humour are 0. This can be implemented using MATLAB thresholding.

Figure 8:
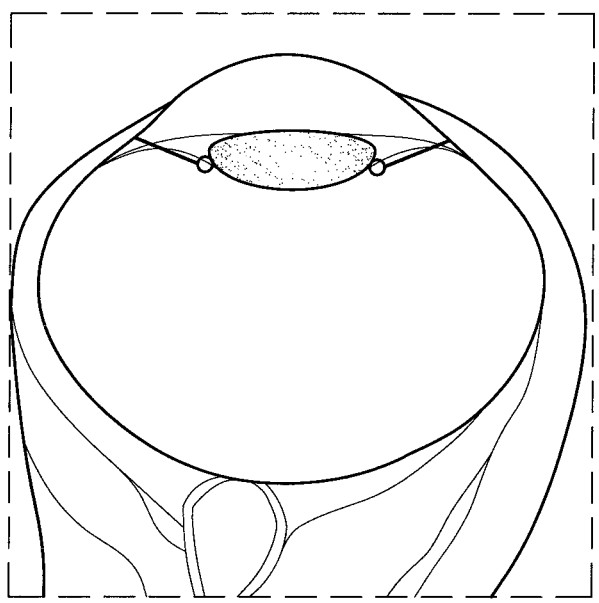
FIG. 8 illustrates estimation of the ciliary muscles according to one embodiment of the invention.

A line with a length that extends beyond the boundary of the eye is drawn from the leftmost edge of the lens towards the left side of the image. This line is swept through an angle of 90° clockwise about the leftmost point in an attempt to search for the attachment point of the ciliary muscles. At each angle, the line starts with a white pixel (since the line originates from the edge of the lens) and improfile is applied to count the number of black pixels along the line on the thresholded image before a second white pixel is found. This roughly represents the thickness of the aqueous humour along the line. Since the ciliary muscles are thresholded and represented by black pixels, it is assumed that the line with the smallest number of black pixels (i.e. narrower aqueous humour due to presence of ciliary attachment) will follow the path of ciliary muscle attachment between the sclera and the lens equator (FIG. 8). The same steps are performed on the rightmost edge of the lens. The angles of the lines obtained from both edges are averaged to get a representative angle of the ciliary muscle ($\theta_{cm}$). This method is typically only performed on the mid-slice which provides a good indication of ciliary muscle attachment points.

As the lens point cloud is sampled for smoothing at each of the sampling angles, the data point that sits on the equator of the smoothed lens is identified. At each sample plane, a line is plotted from the equator point to the boundary of the aqueous humour, such that the line sits at an angle of $\theta_{cm}$. Function meetpoint is used to determine where the line intersects the outline of the eye and the intersection point is recorded as the attachment point of the ciliary muscle on the sclera for each of the sampling angles.

Determine Optic Nerve Head (445):

To determine the optic nerve head, an image slice where the boundary of the optic nerve head is relatively clear is selected. This can be done by an experienced technician, or by a suitably trained neural network. Thresholding is applied to the image slice so that pixels in the optic nerve head region and the boundary around the vitreous humour are labelled as 0.

The 3D ellipsoidal fit to the vitreous humour is used to identify the data points of the vitreous humour fitted boundary on the cross-section of the image slice. A line is drawn from the centre of the fitted vitreous humour towards the bottom edge of the image. Starting from the point where the line intersects the vitreous humour boundary, improfile is applied on the thresholded image along the line towards the bottom edge of the image. The number of continuous pixels that are labelled as 0 on the line is recorded. If the number of pixels is bigger than 3, the line is considered to be within the region of the optic nerve head or attachment. The line is swept through all angles (about the centre of the fitted vitreous humour) to cover the bottom boundary of the vitreous humour. This step may generate multiple bands of lines which are considered as part of the optic nerve attachment. The largest of these continuous bands is chosen to be representative of the optic nerve head or attachment region. The line in the middle of the band represents the axis of the optical nerve and where the line intersects the vitreous humour boundary is assigned as the middle of the optic nerve head or optic disc.

The processed MRI data is used to create an initial 3D "scaffold" point cloud. The tissue boundaries (e.g. lens, optic disc, vitreous humour) detected in the MRI dataset are added as part of the point cloud. These are then 'co-registered' or aligned with same boundaries detected in a secondary imaging modality or second processed image data derived from a different type of imaging process as described in detail below.

Processing of Fundus Photography Images (Second Ocular Image)

Figure 9:
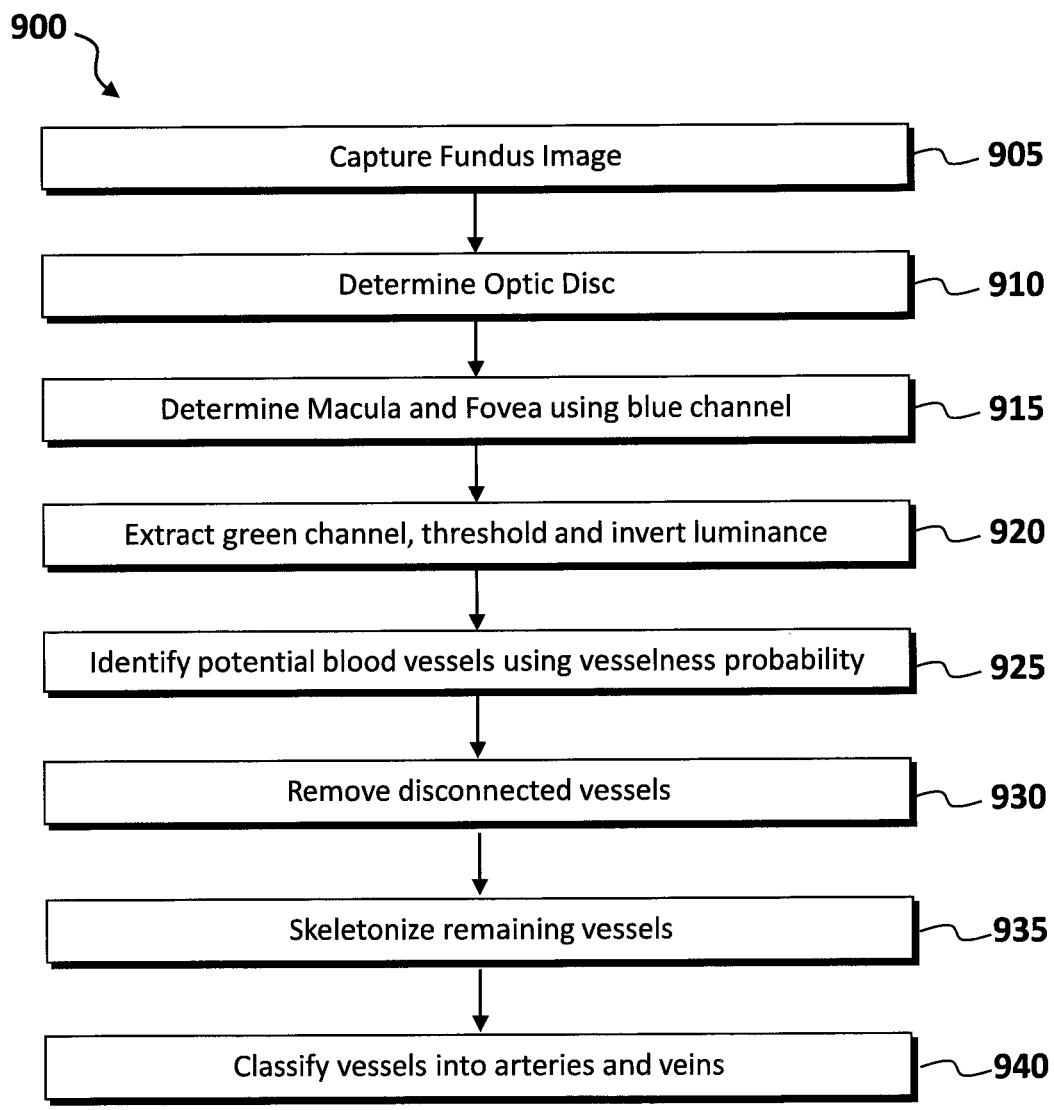
FIG. 9 is a flow chart of a method of processing fundus photograph eye image data to generate fundus photograph processed image data according to one embodiment of the invention.

A method of processing second or fundus photograph eye image data to generate second or fundus photograph processed eye image data according to an embodiment is shown in FIG. 9. The steps of this method (900) are described in more detail below and may be implemented using the processing system 220 of FIG. 3. The fundus photograph eye image data is for the same eye 210 as the MRI eye image data. The fundus image may be captured by specialised photographic equipment and is typically generated as an image in JPEG, PNG, DIACOM or any other raw format. In this embodiment the image data is converted into an integer square matrix for MATLAB image processing (905).

Optic Disc (910):

The red channel of the image is extracted as this may provide a high contrast for visualising the optic disc. The red channel of the image is thresholded so that pixels in the optic disc (high red values) have a value of 1. The thresholded image contains mainly the optic disc which is more circular compared to the other splotches of irregularly shaped islands in the image. Hence, an initial fit of the optic disc to a circle is performed using imfindcircles. To obtain a more accurate fit for the optic disc, a line that extends beyond the boundary of the optic disc is drawn from the centre of the fitted circle towards the bottom edge of the image. Starting from the end outside the optic disc, improfile is applied to the line on the red channel of the image. The location where the value of the red channel increases sharply is recorded as the edge of the optic disc. The line is rotated about the centre of the optic disc until the whole boundary of the optic disc is identified. Edge points returned at each rotation angle are checked against the edge point returned by the previous angle step to ensure that the new point lies reasonably close to the previous point. If the new point is outside a threshold acceptable range, the radius between the previous point and the centre of the fitted circle is used to estimate the position of the new point at the current angle step. The new set of data points which approximates the boundary of the optic disc are then fitted to an ellipse using the fit_ellipse.

Macula & Fovea (915):

The blue channel of the fundus image may provide a high contrast for identifying the macula. The blue channel is thresholded to retain the macula (low blue values). The macula is fitted as a circle using imfindcircles, and the centre of the fitted circle is recorded as the approximate location of the fovea in the fundus image.

Blood Vessels:

Vessel segmentation from the fundus image may be implemented using a modification to the method introduced by Frangi et al "Multiscale vessel enhancement filtering", International Conference on Medical Image Computing and Computer Assisted Intervention, Springer, Berlin, Heidelberg 1998, which is incorporated herein by reference. The Frangi method detects blood vessels using a second order gradient signal change at the vicinity of a vessel within Magnetic Resonance Angiography (MRA) and Computerised Tomography Angiography (CTA) images. This method is adopted for the fundus image which, unlike MRA and CTA images, is in colour. In fundus images, the vessels are a shade of red against a red retinal image. Therefore, the green channel of the image may be extracted as it provides a high contrast between the background and the blood vessels. Pixels with green values below a threshold value are assigned to 0 so as to suppress the background and improve contrast of the blood vessels. Luminance is then inverted so that the blood vessels show up as bright pixels against a dark background in grayscale. (920)

The original Frangi model had been developed on Magnetic Resonance Angiography (MRA) and Computer-assisted Tomography Angiography (CTA) modalities that are low-resolution and contrast by nature. Hence, in its original form, this technique is only capable of detecting relatively large blood vessels. Fundus photos, in contrast, are high resolution and high contrast images, are not based on angiography (dye injection), but are obtained through photography of retinal blood vasculature. Hence, the Frangi model may be optimized here, to be able to detect microvessels that are common in retinal images, accurately (high true positives) and reliably (low false negatives). This optimization is achieved by using the "green" channel of fundus photographs, as well as modifying the "vesselness" measure of the original Frangi method.

A gaussian filter is applied to smooth the image. For each pixel in the image, the Hessian and eigenvalues of the Hessian ($\lambda_1$, $\lambda_2$, where $|\lambda_1|<|\lambda_2|$) are computed. The eigenvalues are used to compute measures:

$$R_B = \frac{\lambda_1}{\lambda_2} \text{ and } S = \sqrt{\lambda_1^2 + \lambda_2^2}.$$

A "vesselness" measure for each pixel is then calculated using:

$$V = \begin{cases} 0, \text{ if } \lambda_2 > 0 \\ \exp\left(-\frac{R_B^2}{2\beta^2}\right)\left(1 - \exp\left(-\frac{S^2}{2c^2}\right)\right), \end{cases}$$

where β and c are threshold parameters which can be determined and adjusted to control the sensitivity of the vesselness filter. The vesselness measure indicates the probability of a pixel being a vessel. Thresholding is then applied and all pixels with a probability higher than the threshold value are assigned as pixels belonging to a vessel. (925)

Modification of the Frangi method for fundus images may result in some "short" vessels that are incorrectly identified as vessels. This is due to the higher resolution and contrast of fundus photographs, and the fact that are true images and not based on angiography (i.e. dye injection). In order to remove these disconnected vessels, bwareaopen is applied to remove all connected components that have less than a defined number of pixels. (930)

Figure 10A:
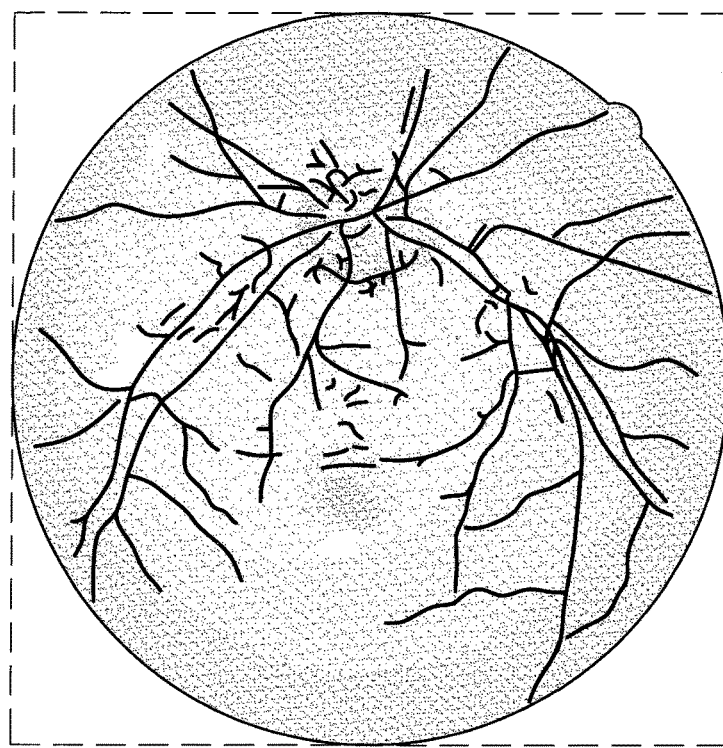
FIG. 10A-B illustrate vessel segmentation and classification in the fundus photograph processed image according to one embodiment of the invention.
Figure 10B:
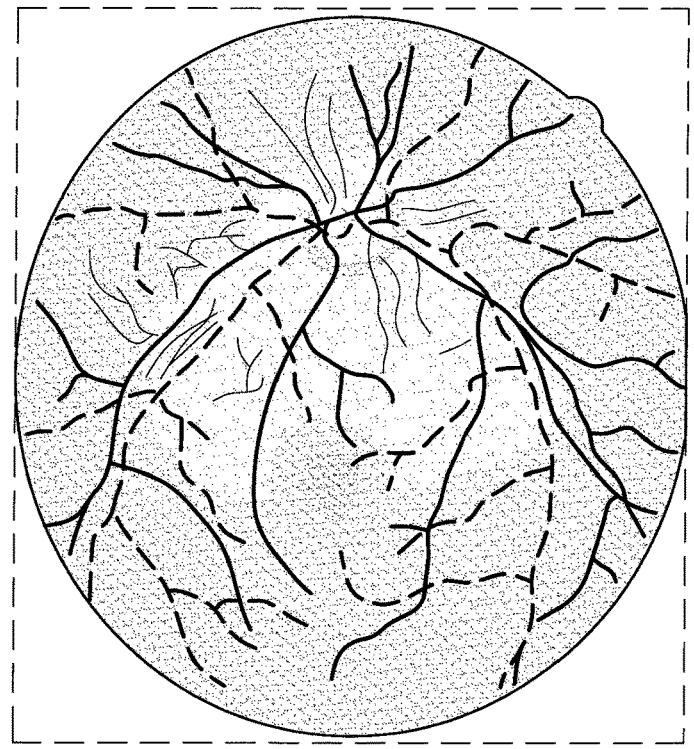

The remaining vessels (FIG. 10*a*) are skeletonized to obtain information about vessel tree connectivity. This can be implemented using the MATLAB bwskel function. (935) Hue values, variance of hue across vessels and calibre of vessel segments are used to automatically classify the segmented vessels into arteries and veins as shown in FIG. 10B (solid lines are arteries and dashed lines are veins). in fundus photography, arteries demonstrate a lighter colour hue compared to the veins. That is because the oxygenated blood inside the arteries is more reflective in the visible range, compared to the venous de-oxygenated blood. Furthermore, arteries are always thinner than the surrounding veins, when imaged by fundus photography. Hue magnitude detection, combined with vessel calibre (thickness), is used to identify the veins from the arteries. Because the arteries and veins both become smaller as their distance from the optic disk increases, the calibre comparison may be done for respective regions of the retina with each region being a predetermined distance range from the optic disc. Vessels below the average calibre for the region are provisionally identified as arteries and those above as veins. The average hue is also determined and if the vessel is both below the average calibre and above the average hue it is confirmed as an artery, otherwise it is classified as a vein. (940)

Combining First and Second Ocular Images to Generate an Ocular Model

Figure 11:
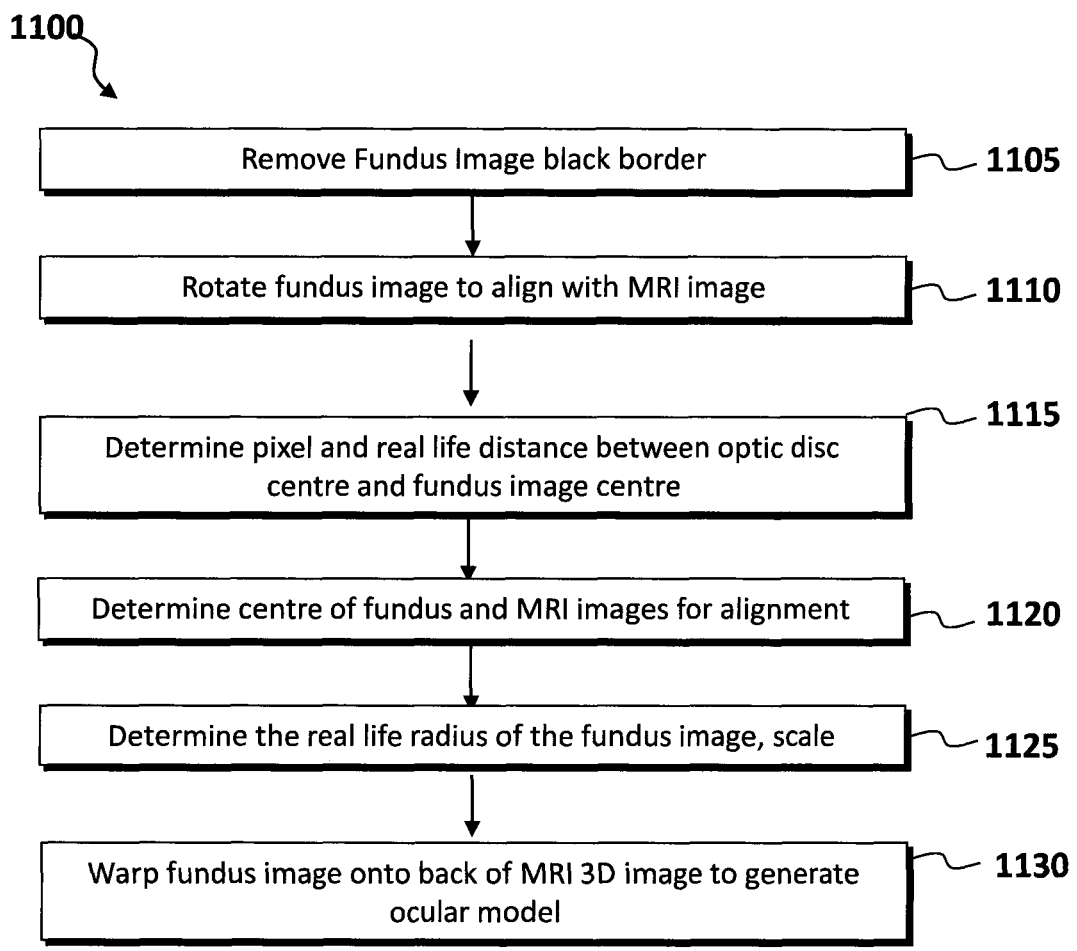
FIG. 11 is a flow chart of a method of combining the processed MRI image data and the processed fundus photograph eye image data to generate an ocular model of the eye according to one embodiment of the invention.

A method of combining the first and second (MRI and fundus photograph) processed image data to generate an ocular model according to an embodiment is shown in FIG. 11. The processed image data (derived from different imaging modalities such as MRI and fundus photography) are processed in point cloud format in the MATLAB image-processing space. The steps of this method (1100) are described in more detail below and may be implemented using the processing system 220 of FIG. 3.

The black border of the fundus image is removed using a mask of the black background converted into a transparent one (1105). The image with a transparent background is saved using imwrite and reloaded again for later use. In order to correctly warp the fundus or second ocular image to the retina of the first ocular image or MRI generated 3D model, the fundus image is rotated so that its optic disc centre and fovea align with the orientation of the optic nerve axis and the optical axis generated in the MRI image.

The centre of the fundus image is identified as the vertical and horizontal mid-points of the eye boundary and is used as the starting point together with a corresponding point on the 3D MRI image to warp or conform the fundus image data to the 3D MRI image. The pixel distance and orientation of the optic disc centre with respect to the centre of the fundus image is computed and the real-life dimensions are derived by multiplying the pixel distance with the pixel resolution of the fundus image (1115). Since the centre location of the optic disc is known in the MRI generated 3D image, the corresponding location of where the centre of the fundus photo sits on the 3D model is calculated. The same real-life distance from the centre of the optic disc to a warping start point is applied in the NT and IS axes in the 3D image. This warping centre point is then translated along the AS axis to the rear boundary of the 3D cloud point. The centre of the fundus image is aligned with the warping centre point (1120)

Figure 12:
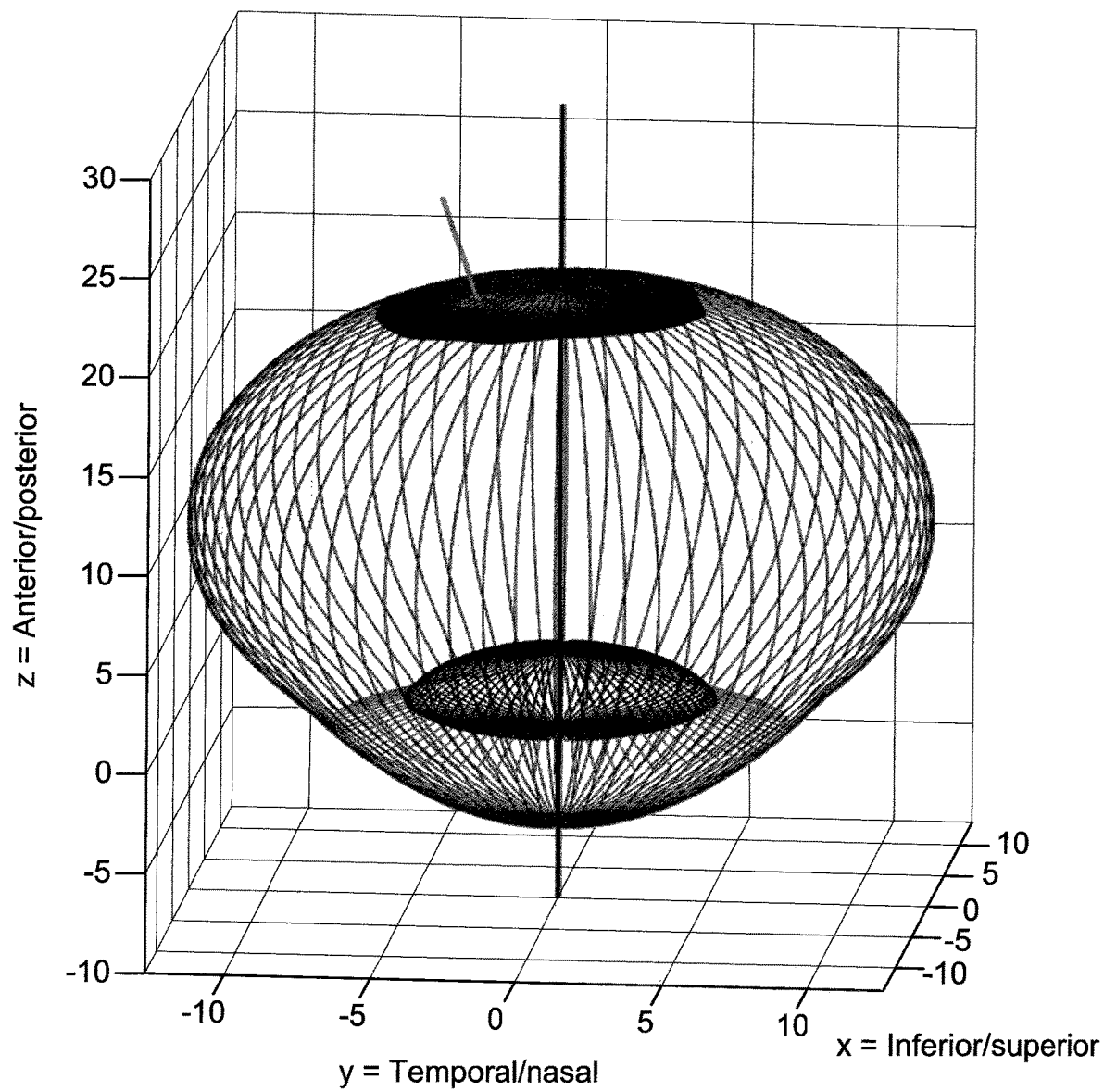
FIG. 12 illustrates alignment and warping of the processed fundus photograph eye image data onto the processed MRI image data according to one embodiment of the invention.

The next step is to determine the real-life radius of the fundus image. This is done by dividing the field of view (FOV as recorded by the camera) by the image pixel size (e.g. 320*320) to obtain real-world pixel sizes (e.g. 1 mm*1 mm). The fundus image is then scaled to the same dimensions as the MRI 3D image using the real-life radius information (1125). From the warping start point on the 3D MRI image, the centre of the scaled fundus image is located then warped onto the back surface as shown in FIG. 12. This can be performed using the MATLAB imwarp function. (1130)

This process leads to warped image data (e.g. from fundus photography) accurately representing the spherical anatomy of the eye. It also includes the co-registered (matched) tissue boundaries from multiple modalities (e.g. fundus and MRI), as well as structures that have been captured by only one of the modalities. For example, the vitreous humour may only be captured by MRI, but correctly represented in relation to the fundus photograph as the retinal boundaries are correctly matched between MRI and fundus photograph.

Processing of OCT Images (Third Ocular Image)

Figure 13:
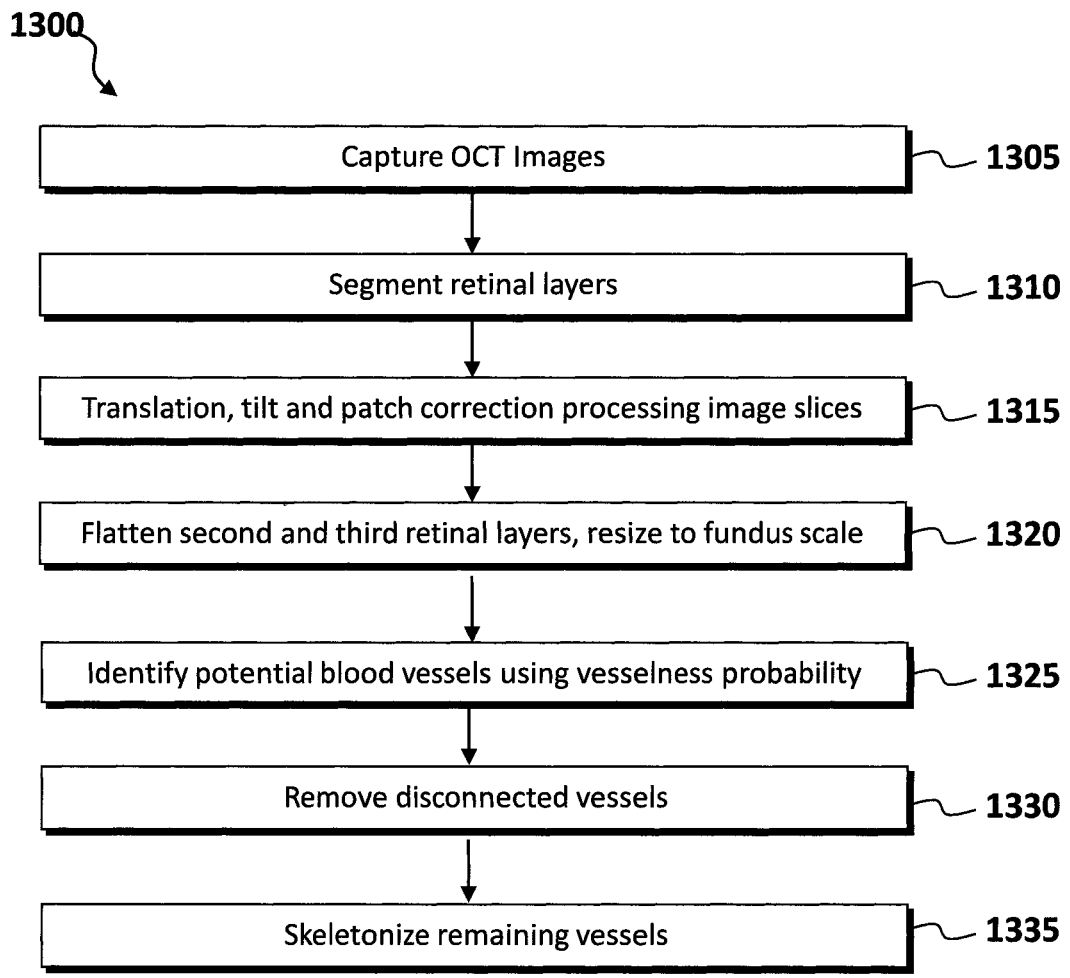
FIG. 13 is a flow chart of a method of processing OCT eye image data to generate OCT processed image data according to one embodiment of the invention.

A method of processing third or OCT eye image data to generate third or OCT processed image data according to an embodiment is shown in FIG. 13. The steps of this method (1300) are described in more detail below and may be implemented using the processing system 220 of FIG. 3.

Figure 14A:
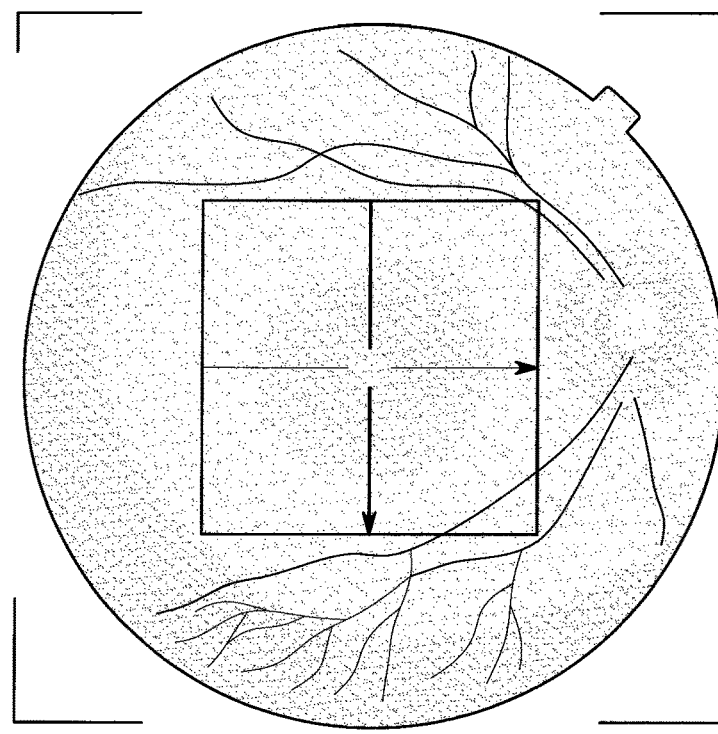
FIG. 14A-B illustrate an OCT scan window and image slice according to one embodiment of the invention.
Figure 14B:
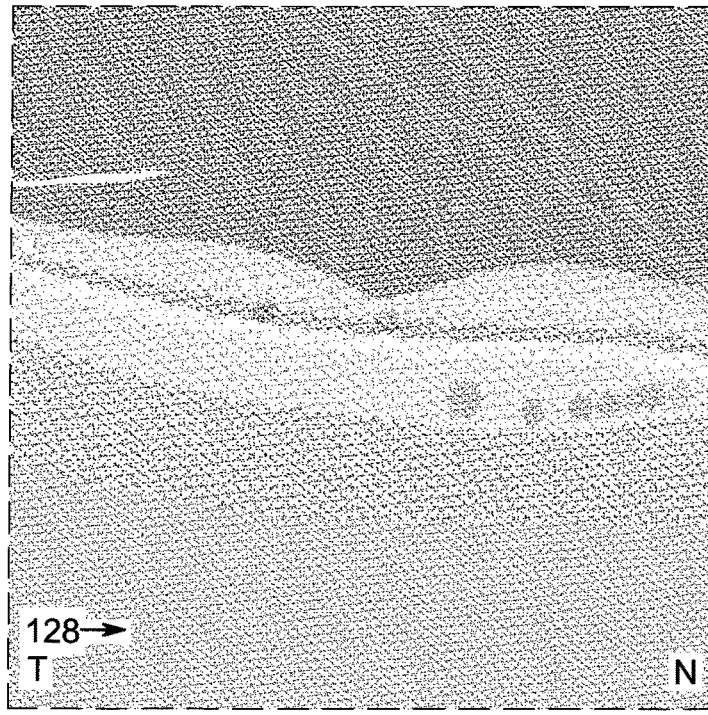

Optical coherence tomography (OCT) uses coherent light to capture micrometre resolution 2D and 3D images from within optical scattering tissue. The imaging information from such scans can be added with the ocular model to further enhance its effectiveness. In this embodiment OCT scans are taken from the superior to inferior of the eye (1305). Current scan protocols use a scan area of 6 mm×6 mm (FIG. 14A) which generates 320 OCT images per patient eye. Pixel intensity data for each OCT (FIG. 14B) image slice is determined. For OCT scans, segmentation of retinal layers is performed by software that is provided as a standard OCT device tool and is typically saved in json format (1310). Coordinates of each retinal layer are imported as a point cloud.

Starting from the second OCT image slice, the OCT image slice is translated so that the right edge of the first retinal layer matches the right edge of the first retinal layer on the previous OCT slice. After translation, a further step is introduced to correct for tilt between image slices. The image and its corresponding layer information are rotated such that the line between the left edge (first point) and right edge (last point) of the first retinal layer aligns with the same line on the previous image slice. When image slices are put together, patches with zero intensity can sometimes arise at the edges due to the correction step. For pixels in these patches, a number between 1 and 40 (low intensity) is generated using a random number generator (randi) and assigned as the intensity of the pixel. This is performed to "fill up" these patches to avoid having these patches picked up as vessels in later stages. (1315)

Retinal blood vessels are generally located between the second and third retinal layers. To identify the location of retinal blood vessels over the 2D scan area, flattening is performed by averaging the intensity of pixels lying between the second and third layer along each pixel column on each image slice. The OCT scan area is then resized to match the scale of the fundus image (1320). When the average intensity of pixels along the second and third layers is plotted over the resized OCT scan area, retinal blood vessels show up as brighter pixels. The same vessel segmentation method employed for fundus image can be applied to the average intensity plot to extract pixel coordinates of the blood vessels in the OCT image (1325, 1330, 1335—refer the description of steps 925, 930, 935 for more details).

After correction has been performed for all image slices, coordinates of the retinal layers are used to generate a 3D point cloud for retinal layers.

Processing of OCTA and/or LS Images (Fourth Ocular Image)

Figure 15:
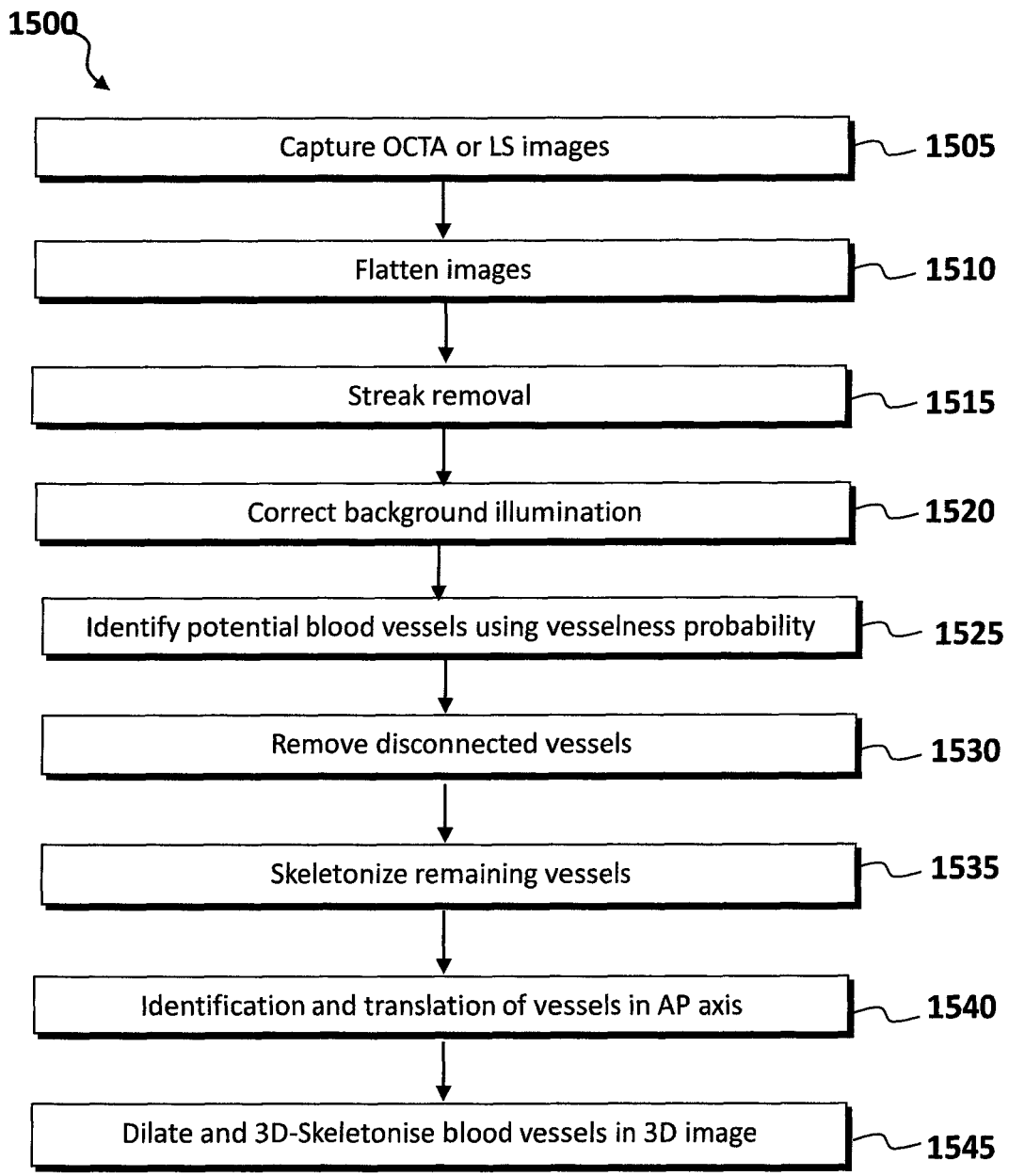
FIG. 15 is a flow chart of a method of OCTA or LS eye image data to generate PCTA or LS processed image data according to one embodiment of the invention.

A method of processing fourth and fifth or OCTA and LS eye image data to generate fourth and fifth or OCTA and LS processed image data according to an embodiment is shown in FIG. 15. The steps of this method (1500) are described in more detail below and may be implemented using the processing system 220 of FIG. 3.

Optical coherence tomography angiography (OCTA) uses laser light reflectance of the surface of moving red blood cells for imaging the microvasculature of the retina and choroid. Typically, multiple OCT scans are conducted across a region to generate a 3D point cloud. This region is scanned repeatedly, and the differences analysed to detect zones of high flow rates. OCTA uses amplitude decorrelation and phase variance to detect motion or blood flow. Laser speckle (LS) imaging visualises tissue blood perfusion and uses backscattered light to form an interference pattern. A changing pattern corresponds to red blood cells moving over time. The OCTA equipment segments the image into retinal layers. Current LS equipment generates a 2S view of the retinal vasculature. Both OCTA and LS provide very high-resolution images of retinal circulation.

Figure 16A:
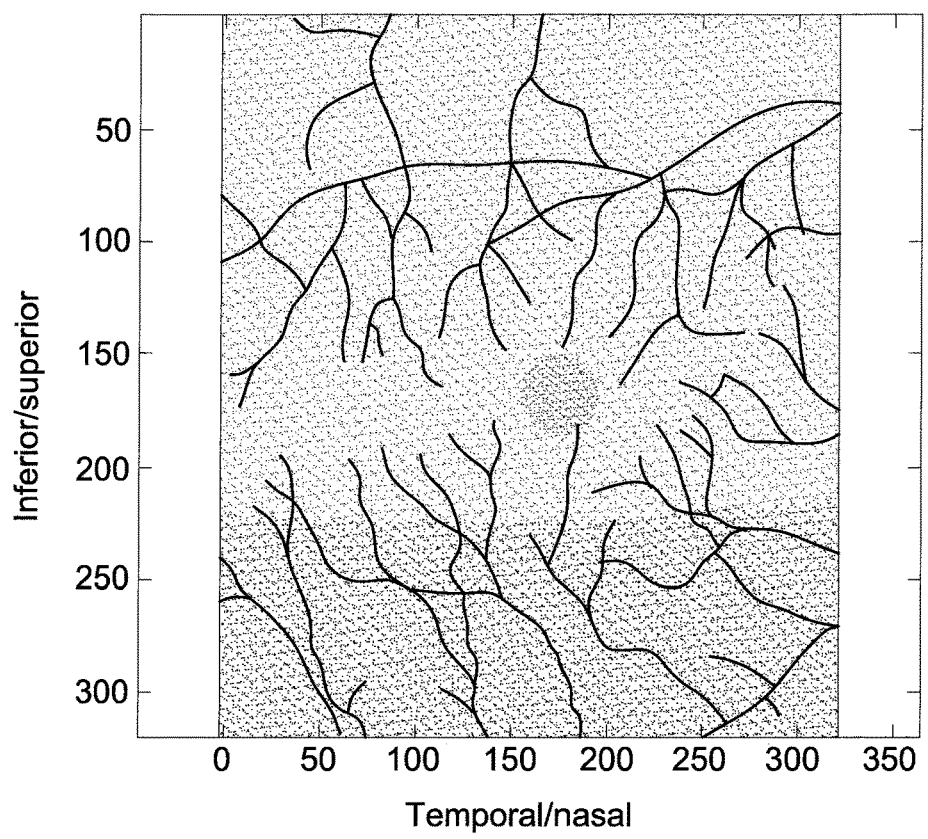
FIG. 16A-C illustrate a flattened retinal perfusion image, 2D vasculature map, and 3D retinal vasculature according to one embodiment of the invention.
Figure 16B:
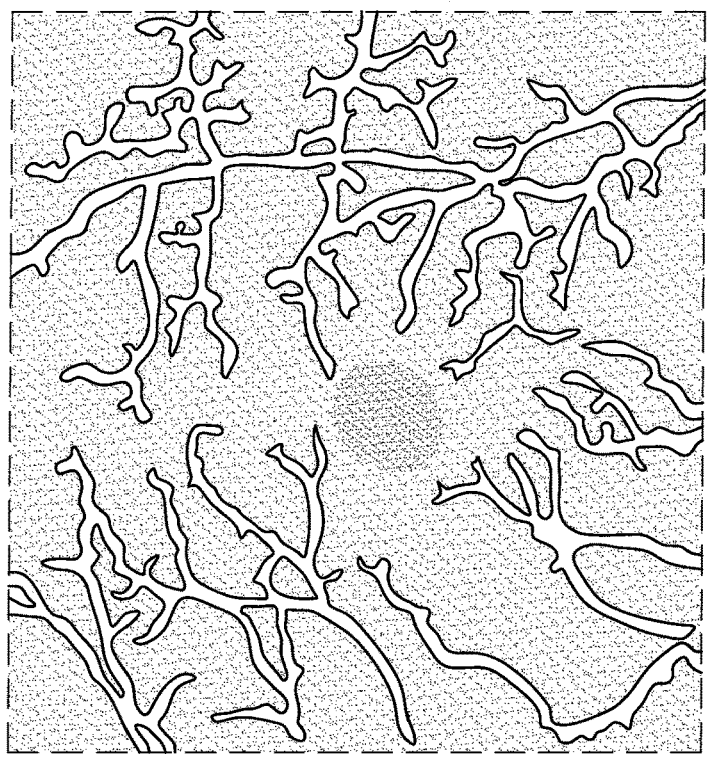

In this embodiment, the 3D OCTA or LS point cloud images are flattened through averaging the pixel intensities between the second and third layers of the retina (1510). In some instances, image flattening can give rise to bright horizontal streaks across the flattened image, which may lead to false identification of blood vessels (FIG. 16A). To remove these horizontal streaks, pixel intensity is summed across each pixel row of the flattened image. Function peakfinder is used to identify rows with local maxima sum intensity, that is local peaks significantly larger than the surrounding area. Each of these identified rows is replaced by the average intensity of pixels on the rows directly above and below it (1515). As flattened images often present uneven illumination, morphological opening (imopen) is used to estimate background illumination, followed by subtraction from the flattened image to correct for uneven illumination (1520). Thereafter, the same vessel segmentation method (1525, 1530, 1535—refer 925, 930, 935 for more detail) employed for the fundus image is applied to the flattened images to obtain a 2D retinal vasculature map based on OCTA or LS images (FIG. 16B).

The resultant vasculature map provides an indication of the 2D location of vessels with respect to the nasal/temporal (NT) and inferior/superior (IS) axes. To map out vessel locations in 3D, the location of where blood vessels sit along the anterior/posterior (AP) axis may be identified. Smoothing (smooth3) may be first applied to the 3D point cloud in order to remove imaging artefacts of OCTA or LS images. Objects fewer than 5 pixels may be removed from the smoothed 3D point cloud using bwareaopen. As the NT and IS locations of each blood vessel pixel is known from the 2D vessel map, pixels along the AP axis with the same NT and IS location may be extracted from the 3D LS or OCTA point cloud and the pixel with the maximum intensity may be marked as the location of the blood vessel in the AP direction (1540).

Figure 16C:
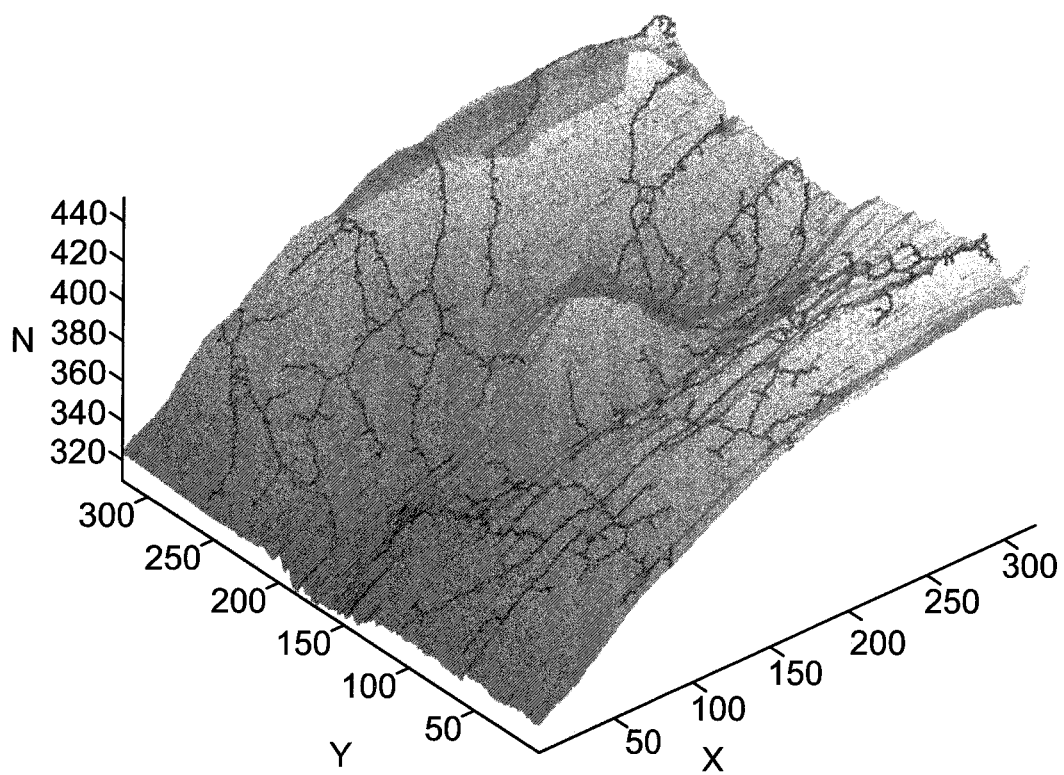

At this stage, the extracted coordinates of the blood vessels in 3D may be disjointed and uneven. Function imdilate is implemented to dilate 'blood vessel' pixels so that neighbouring points that were disjointed before are now connected. A skeletonisation function for processing 3D data (Skeleton3D) is then applied to obtain the path of blood flow through the vascular network (1545) (FIG. 16C).

Adding OCT, OCTA, LS Processed Image Data to the Ocular Model

Figure 17:
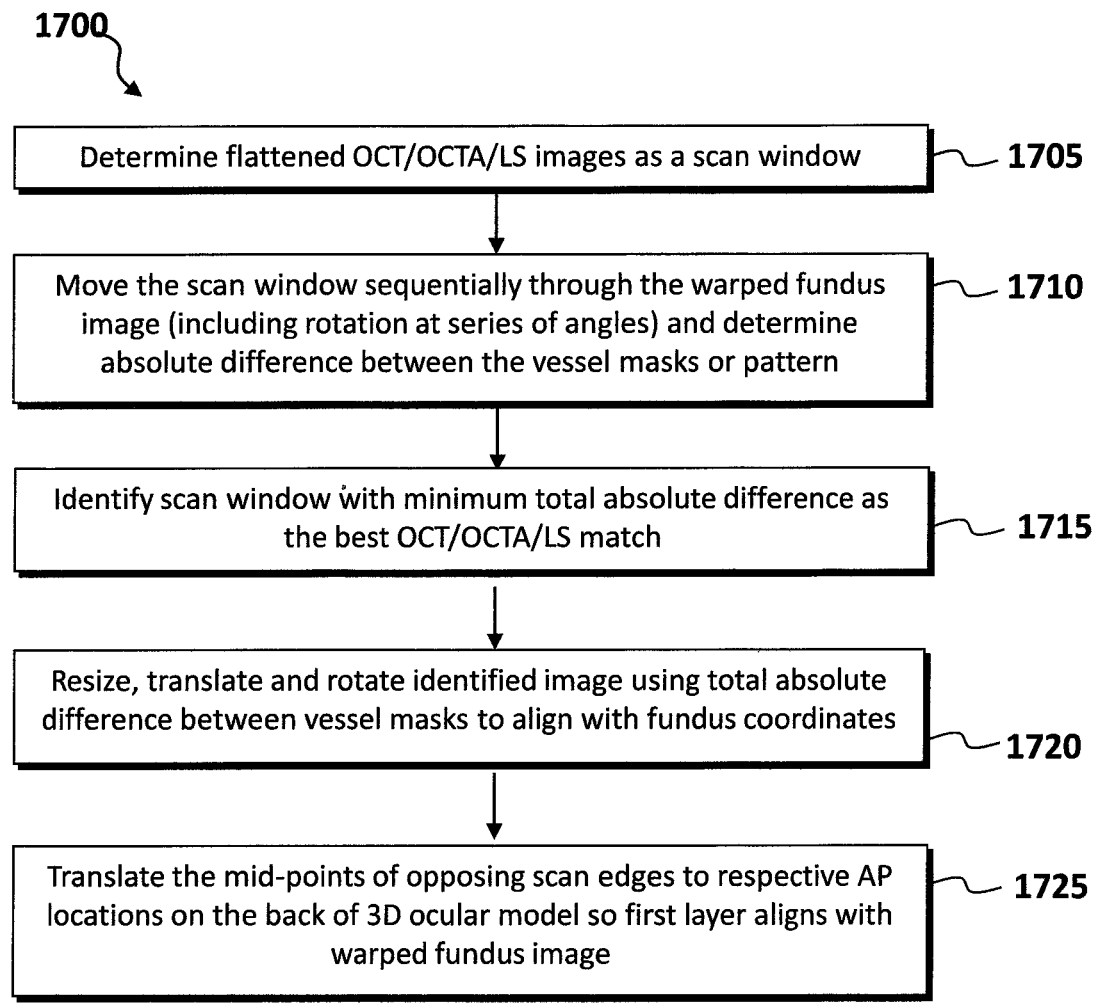
FIG. 17 is a flow chart of a method of adding the processed OCT, PCTA and/or LS image data to the ocular model of the eye according to one embodiment of the invention.

A method for adding the third, fourth and/or fifth (OCT, OCTA and/or LS) processed image data to the ocular model according to an embodiment is shown in FIG. 17. The steps of this method (1700) are described in more detail below and may be implemented using the processing system 220 of FIG. 3.

Figure 18A:
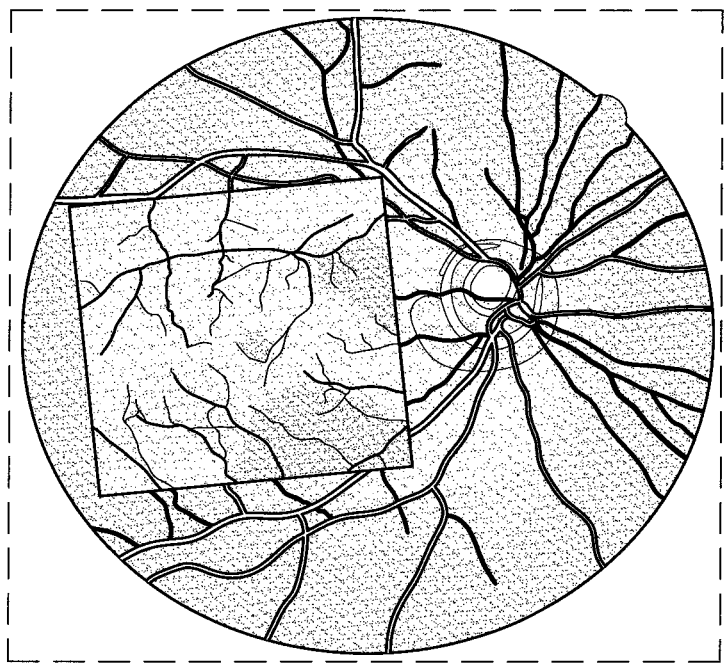
FIG. 18A-D illustrate an OCT scan window and the retinal layers transformed to ocular model coordinates and overlaid according to one embodiment of the invention.

Having processed OCT, OCTA and LS images to retrieve data on retinal layers and vasculature, the next step is to register the image data with the other eye image data making up the ocular model, for example to orientate the data within the ocular model. The averaged (flattened) OCT, OCTA and LS image (1705) registration is performed using the warped fundus image of the same eye as a reference. This is achieved by matching the vasculature pattern between the flattened OCT images and the warped fundus image. This process involves a scan window corresponding to the flattened OCT image being moved sequentially through the space of the warped fundus image. At each location, the scan window is rotated through a series of angles, for example between −6° to 6°. The scan window is superimposed over the vessel mask or pattern derived from the fundus image, and the absolute difference between the vessel mask in the scan window and the fundus vessel mask is calculated at all points. In other words, the vessel mask in the flattened OCT image is subtracted from the vessel mask in the warped fundus image (1710). The scan window with the minimum total absolute difference is deemed as the window on the fundus image which produces the closest match to OCT vessel map (1715) (FIG. 18A). These steps can be repeated for OCTA and LS datasets. Furthermore, OCT/OCTA/LS scans of different regions of the eye (e.g. macula and optic disc) can be combined (stitched) in this manner. In other words, scans of different areas of the retina can be stitched together to generate a fuller point cloud or ocular model. The same vessel pattern matching process can be used to ensure correct alignment within the ocular model.

Figure 18B:
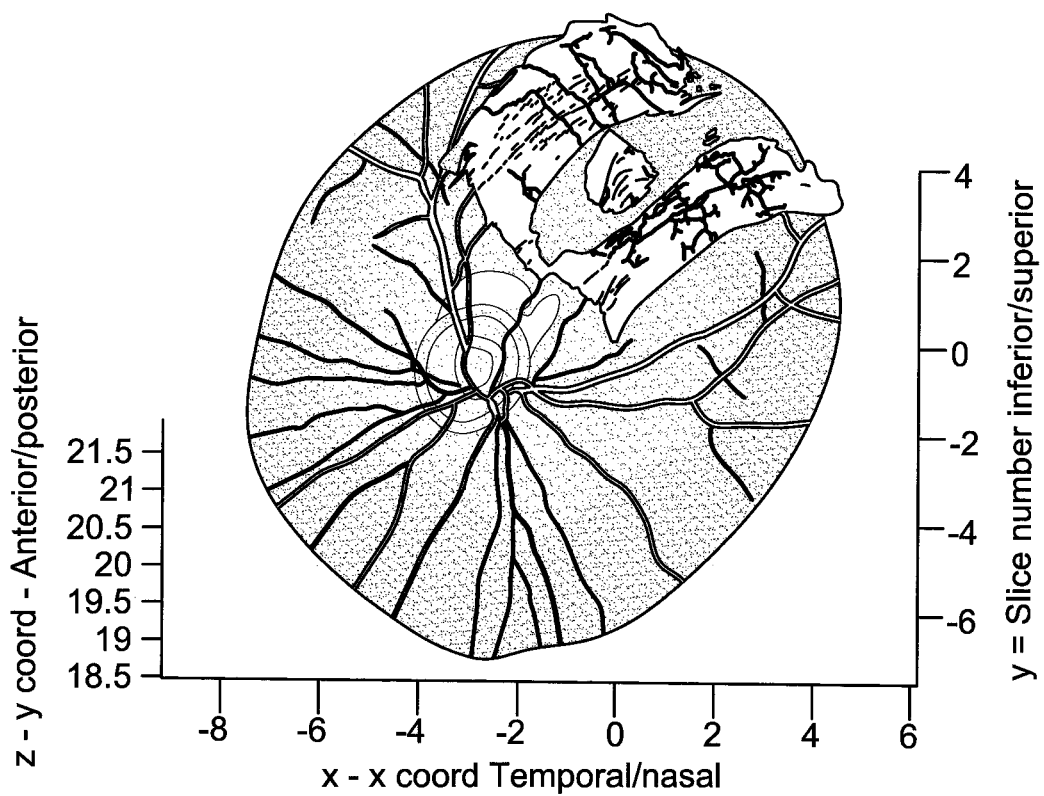

Using the midpoint and angle of the scan window with the closest match, the retinal layer and vasculature point cloud derived from the OCT, LS and OCTA images are then transformed (resized, translated, rotated) to the same coordinate system as the fundus image using the vessel pattern or masks. The selected OCT/OCTA/LS image is resized to minimise the absolute difference between the vessel masks of the fundus and selected OCT/OCTA/LS images. The OCT image is also translated and rotated using the same method so that the absolute difference between the vessel masks is zero or very close (1720). The same transformation steps as described in relation to steps 1110-1125 in FIG. 11 are applied to further convert the OCT, LS and OCTA point cloud to the coordinate system of the ocular model. These steps will align OCT, OCTA or LS data with respect to the NT and IS axes. FIG. 18B shows the overlay of retinal vasculature over the warped fundus image.

Figure 18C:
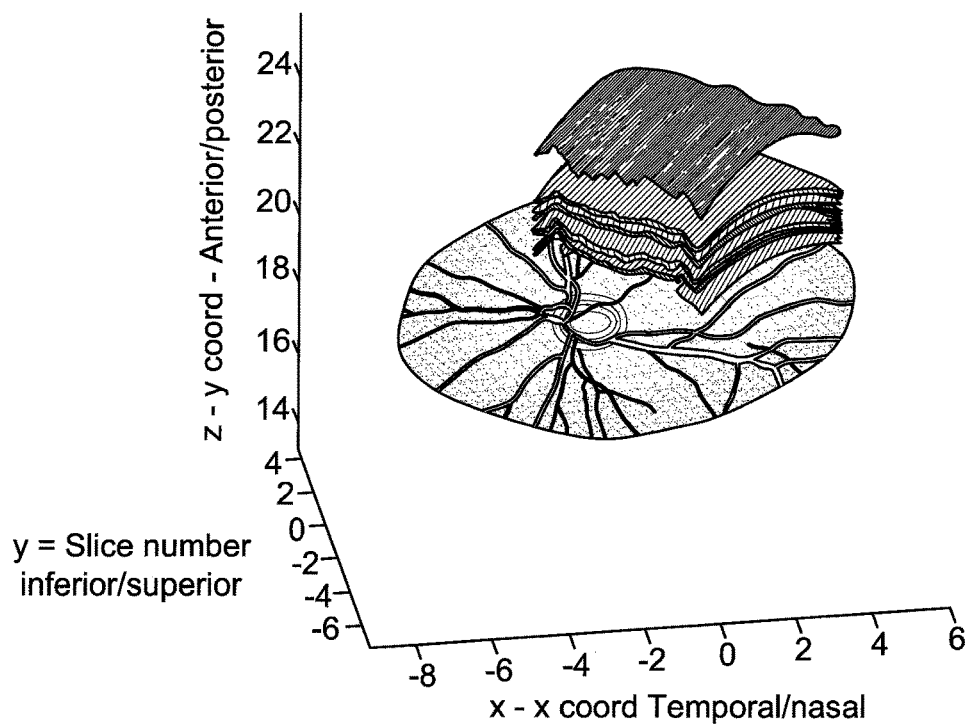
Figure 18D:
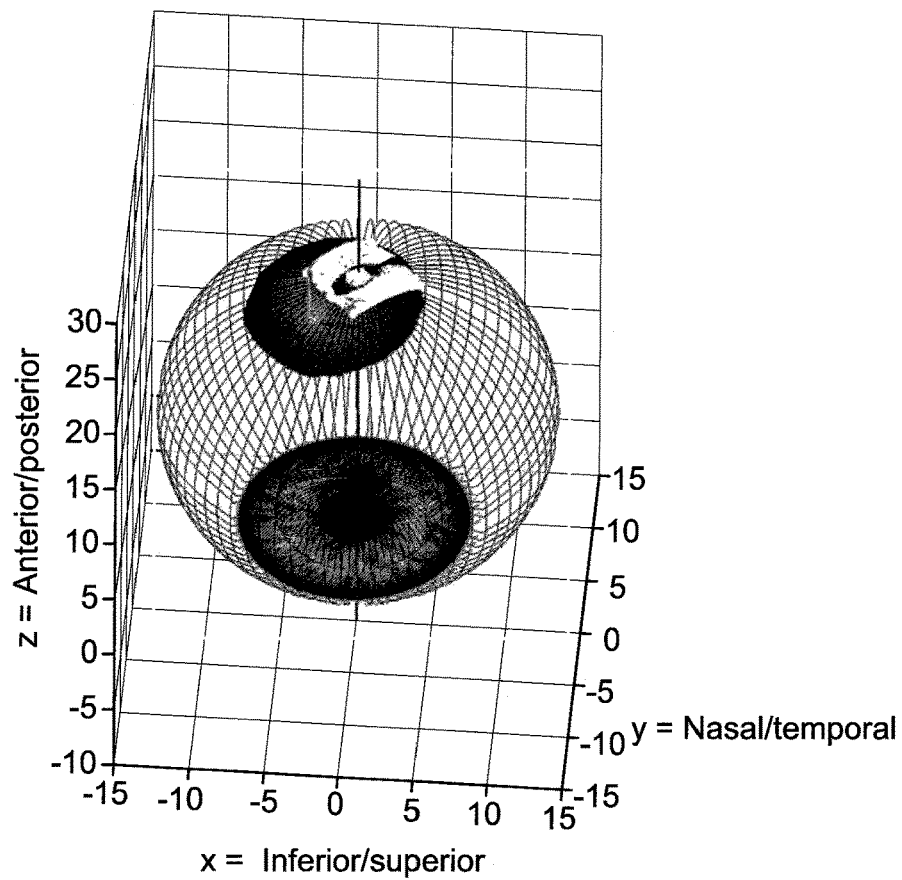

The edge of the selected OCT scan area that is nearest to the optic disc is identified. The entire un-flattened OCT retinal layer point cloud is translated along the AP axis such that the mid-point of that edge on the first retinal layer ($x_1$, $y_1$, $z_{OCT1}$) is aligned to the back surface of the 3D eye model ($x_1$, $y_1$, $z_{fundus1}$) where the fundus image was warped—i.e. their AP locations align. To conform the retinal layers to the back surface of the 3D eye model, the entire retinal layer point cloud is rotated such that the midpoint on the opposite edge ($x_2$, $y_2$, $z_{OCT2}$) aligns with ($x_2$, $y_2$, $z_{fundus2}$) on the back surface of the 3D eye model (1725). FIG. 18C shows the overlay of retinal layers over the warped fundus image. The same set of transformation (i.e. resizing, translation and rotation) is performed on the retinal vasculature 3D point cloud of the OCTA and LS images. FIG. 18D shows the overlay of the second retinal layer and vasculature over the fundus image on the 3D eye model.

General Combining of Image Data in an Ocular Model

The ocular model may comprise any two or more of the above described types of processed image data. In addition or alternatively, the ocular model may comprise processed image data derived from different imaging processes not specifically described above. These may include X-ray, CT, ultrasound, biometry, refractometry, or other techniques known to those skilled in the art. The ocular model may be used for diagnosis, treatment planning and prognosis including but not limited to the methods described below. The ocular model may also be used for visualisation of the eye, training of medical staff, surgeon training, and robotic surgery.

There has been described a computer-implemented image processing method for generating data representative of a model of an eye, or virtual eye model. A processor receives first eye image data of the eye, where the first eye image data is obtained from a first imaging modality. In this context a "modality" is understood to be a process for obtaining image data and/or a type of image data obtained. Examples of modalities are provided elsewhere in this specification.

The first eye image data is processed to generate first processed eye image data. Any manner of image processing steps may be performed to process the eye image data, for example those described in this specification and any known to the skilled addressee. Processing the eye image data may identify one or more features of the eye. The features of the eye may be any anatomical, physiological and/or functional features or characteristics of the eye, for example the examples given in this specification. The modality used to obtain the first eye image data may indicate a particular type of eye features (e.g. anatomical, physiological and/or functional).

The processor also receives second eye image data, which is obtained from a different modality from the first eye image data. Similar processing of the second eye image data occurs to identify anatomical, physiological and/or functional features of the eye. Further eye image data (third, fourth, etc, eye image data) may similarly be received and processed in a similar manner.

The first processed eye image data and the second processed eye image data is registered. That is, like features in the first processed eye image data and the second processed eye image data are identified and the processed image data is manipulated in some way to align or otherwise match the images represented by each set of data.

The registered first and second processed eye image data is then combined to generate data representative of a model of the eye. The data representative of the model of the eye may be output. Outputting this data, or any other data or parameter described in this specification, may comprise, for example, sending the data over a communications link and/or saving the data on a data storage medium.

Anisotropy Maps of Retinal Perfusion

Figure 19:
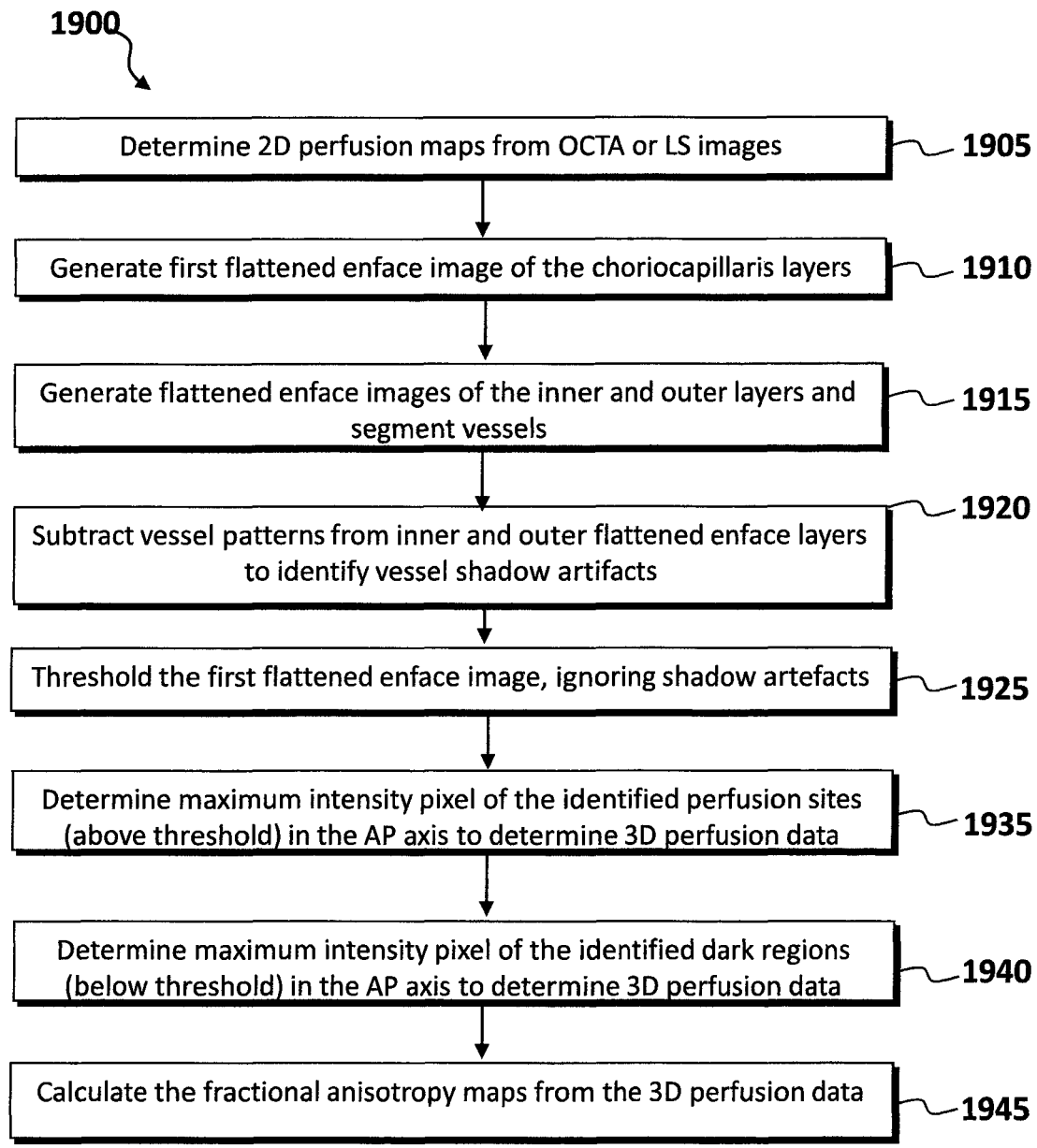
FIG. 19 is a flow chart of a method of determining anisotropy maps of retinal perfusion according to one embodiment of the invention.

A method of determining physiological data related to an eye is described below, in particular determining anisotropy maps of retinal perfusion. The steps of this method (1900) are described in more detail below with reference to FIG. 19 and may be implemented using the processing system 220 of FIG. 3.

Figure 20A:
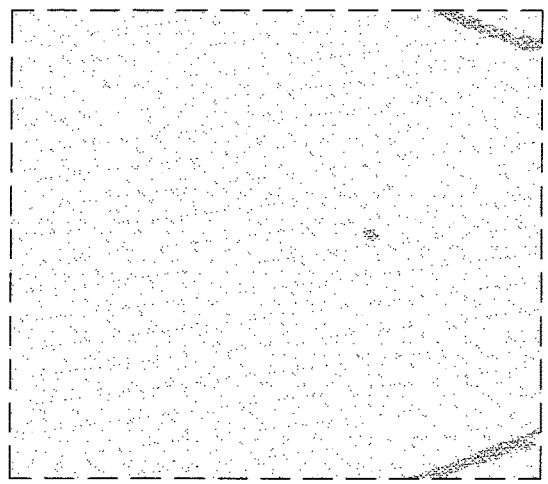
FIG. 20A-C illustrate enface representations of choriocapillaris perfusion according to one embodiment of the invention.

In this embodiment retinal perfusion maps in the choriocapillaris are generated from 3 mm×3 mm OCT and OCTA scans as is known (1905). The Bruch's membrane (BM) is identified through segmentation performed by proprietary software supplied on the OCT scanner. The thickness of the choriocapillaris ranges from 10-23 microns below the Bruch's membrane. OCT-A images within the above range are then selected to obtain enface images of layers of the retina. The OCT-A images may be selected manually, by a trained neural network, or may be defined by a predetermined area of the retina. Each enface image is a cross-sectional compositional image derived from the OCT-A image slices at a given depth of the retina. The enface images may be generated by software tools available with the OCT scanner equipment. The enface images are averaged to obtain flattened enface representations of the multiple layers of choriocapillaris perfusion within the 10-23 micron range (1910) (FIG. 20A). It will be understood that other ranges could alternatively be used.

Figure 20B:
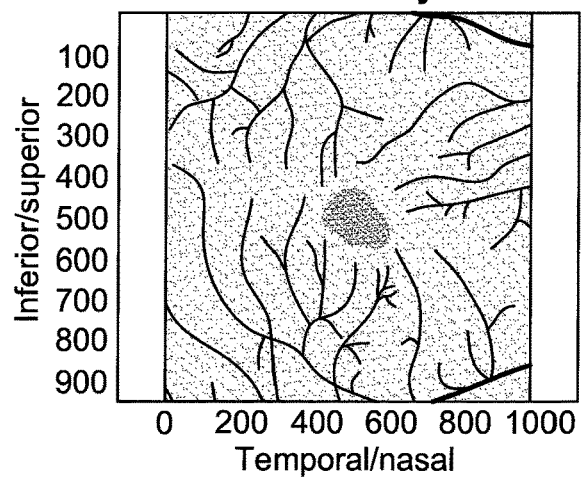
Figure 20C:
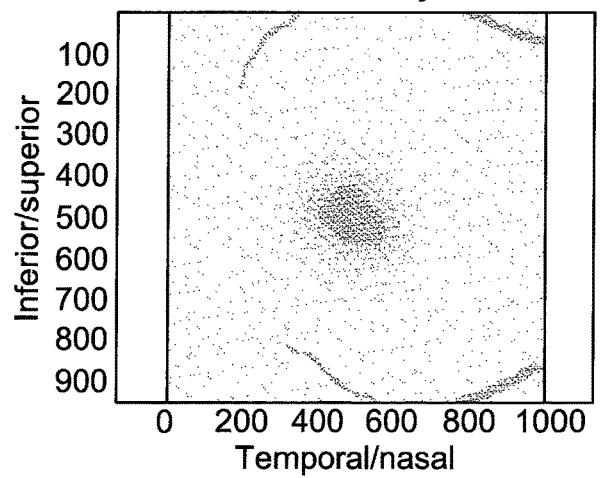

However, artefacts caused by shadows of thicker retinal vessels can sometimes be found on the enface representation of choriocapillaris perfusion. To correct for these shadow effects, retinal blood vessels are segmented using a flattened enface representation of two or more inner retina layers, and as described in steps 925, 930, 935 (FIG. 20B). These vessels usually re-appear as darker vessels in deeper layers. To identify these vessels, a second flattened enface image is obtained by averaging the pixels within two or more outer retinal layers, and darker vessels are segmented as described in steps 925, 930, 935 (FIG. 20C) (1915). If the same vessel is segmented on both enface images, the vessel is marked as a retinal blood vessel that has cast a shadow in deeper layers. This can be determined by subtracting the two vessel masks to identify the differences, then subtract again the differences from the first image to identify the common vessels (1920). The enface image of choriocapillaris is thresholded to identify dark regions with low pixel intensity. Pixels with low intensity which coincide with pixels that had been marked as shadows are assigned as shadows artefacts in the enface image of the choriocapillaris. These pixels that are identified as shadow artefacts are not used in future analysis of OCTA data.

Figure 21:
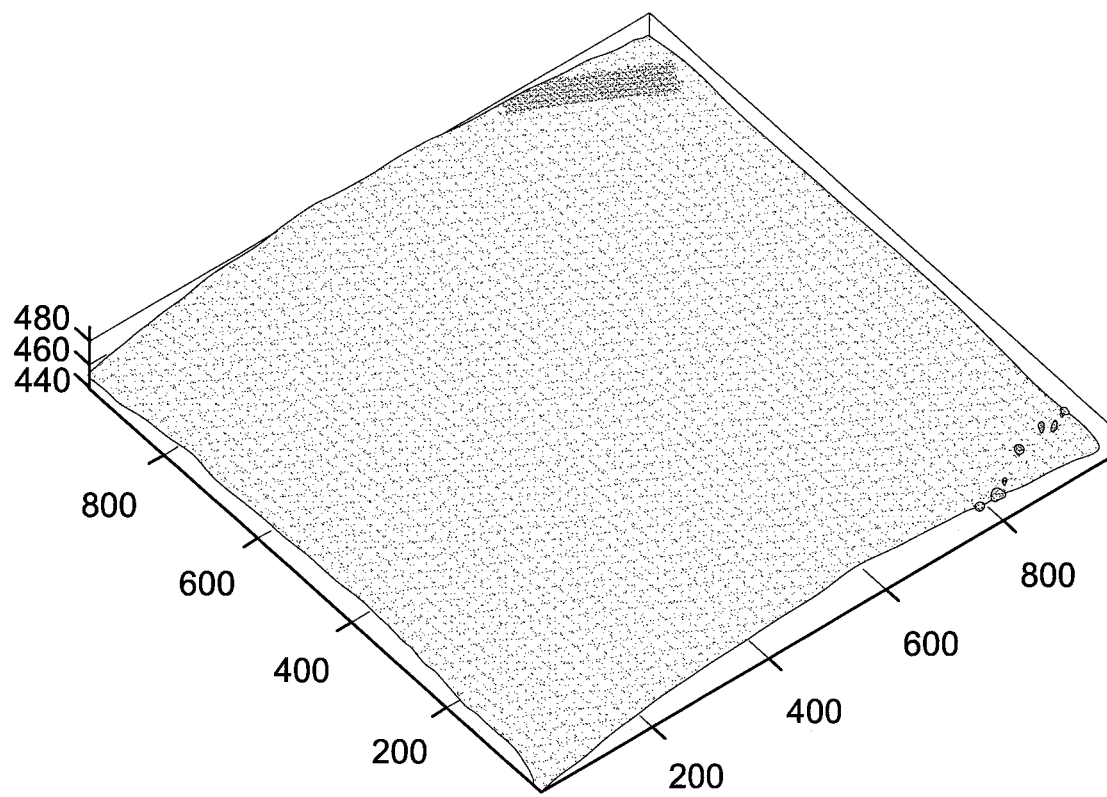
FIG. 21 illustrates a 3D representation of choriocapillaris perfusion according to one embodiment of the invention.

As perfusion in the choriocapillaris is represented as bright regions, the enface image of the choriocapillaris is thresholded to identify pixels with an intensity above a threshold value to identify perfusion (1925). Since the NT and IS locations of each of these perfusion pixels is known from the enface image of the choriocapillaris, pixels with the same NT and IS location lying between the BM and a predetermined number of pixels (depending on the scanner used) beneath the BM along the AP axis are extracted from the 3D OCT-A point cloud. The pixel with maximum intensity is marked as the AP location where choriocapillaris perfusion occurred (1935). This method is described in more detail in relation to step 1540. By repeating the same procedure for all perfusion pixels, a 3D representation of choriocapillaris perfusion (FIG. 21) is obtained.

Regions below the threshold intensity are attributed to perfusion voids or shadows. For shadow regions, it may be assumed that shadow pixels behave similarly to their surrounding pixels. These shadow pixels are excluded from the anisotropy calculations since they are considered to be isotropic. Then the same method is applied to detect the AP location of the pixel with maximum intensity (1940). This will ensure that the shadows are not mistakenly identified as areas of devascularisation within the choriocappliaris.

Calculating Fractional Anisotropy (FA) for Choriocapillaris Perfusion

Figure 22:
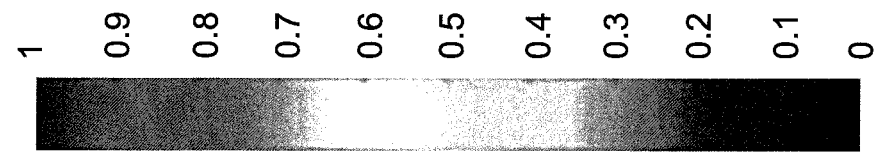
FIG. 22 illustrates an anisotropy map of retinal perfusion according to one embodiment of the invention.
Figure 22:
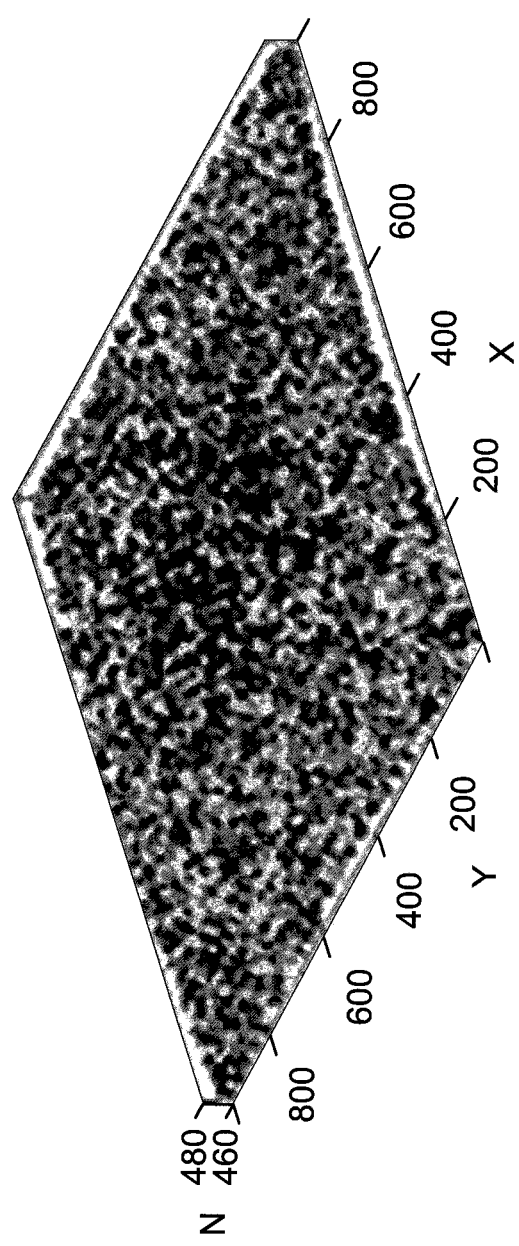

To quantify homogeneity of perfusion in the choriocapillaris, fractional anisotropy (FA) is applied to the OCTA (or LS) datasets and is calculated for each perfusion pixel. An FA value of 1 indicates anisotropic perfusion around the pixel which suggests that perfusion occurs mainly along one direction. An FA value of zero refers to isotropic perfusion around the pixel, implying that perfusion is either uniformly present or absent in all directions. FA is calculated from eigenvalues $\lambda_1$, $\lambda_2$, $\lambda_3$. For each perfusion pixel $(x_p, y_p, z_p)$, its neighbouring pixels are checked to identify perfusion pixels, for example in one embodiment the 26 neighbouring pixels are checked. If a neighbouring pixel is a perfusion pixel $(x_n, y_n, z_n)$, the absolute difference between the coordinates of the neighbouring perfusion pixel and the perfusion pixel is calculated ($|x_p-x_n|$, $|y_p-y_n|$, $|z_p-z_n|$). A weightage, for example 0.5, is then applied to the difference. The weighted difference in x-coordinates is added to $\lambda_1$, weighted difference in y-coordinates added to $\lambda_2$, and weighted difference in z-coordinates to $\lambda_3$, respectively. FA is then calculated for the perfusion pixel $(x_p, y_p, z_p)$ using:

$$FA = \sqrt{\frac{3}{2}} \frac{\sqrt{(\lambda_1 - \hat{\lambda})^2 + (\lambda_2 - \hat{\lambda})^2 + (\lambda_3 - \hat{\lambda})^2}}{\sqrt{\lambda_1^2 + \lambda_2^2 + \lambda_3^2}}$$

where $\hat{\lambda}$ is the mean eigenvalue given by $\hat{\lambda}=(\lambda_1+\lambda^2+\lambda_3)/3$. FA is calculated for each perfusion pixel to generate the distribution of FA (FIG. 22) (1945).

Alternatively or additionally the following parameters may be calculated to determine anisotropy maps of retinal perfusion Relative Anisotropy (RA):

RA is similar to FA but can be less prone to image noise.

$$RA = \frac{\sqrt{(\lambda_1 - \lambda_2)^2 + (\lambda_1 - \lambda_3)^2 + (\lambda_2 - \lambda_3)^2}}{\lambda_1 + \lambda_2 + \lambda_3}$$

Volume Ratio (VR):

VR represents the ratio of the ellipsoid volume to the volume of a sphere of radius ($\lambda$), its range is from 1 (isotropic diffusion) to 0.

Figure 23:
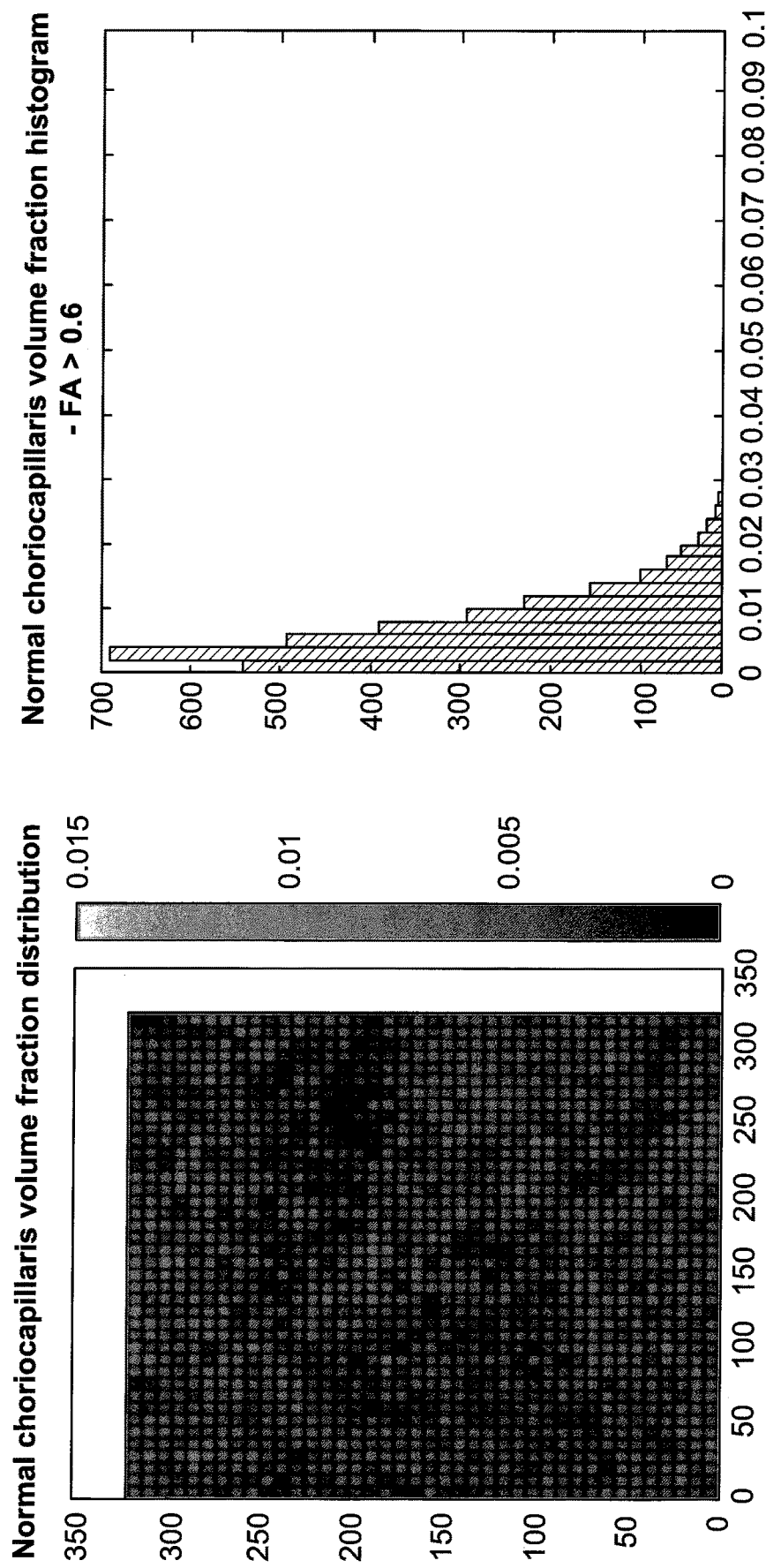
FIG. 23 illustrates a retinal perfusion map and an anisotropy map of retinal perfusion for a normal eye.
Figure 24:
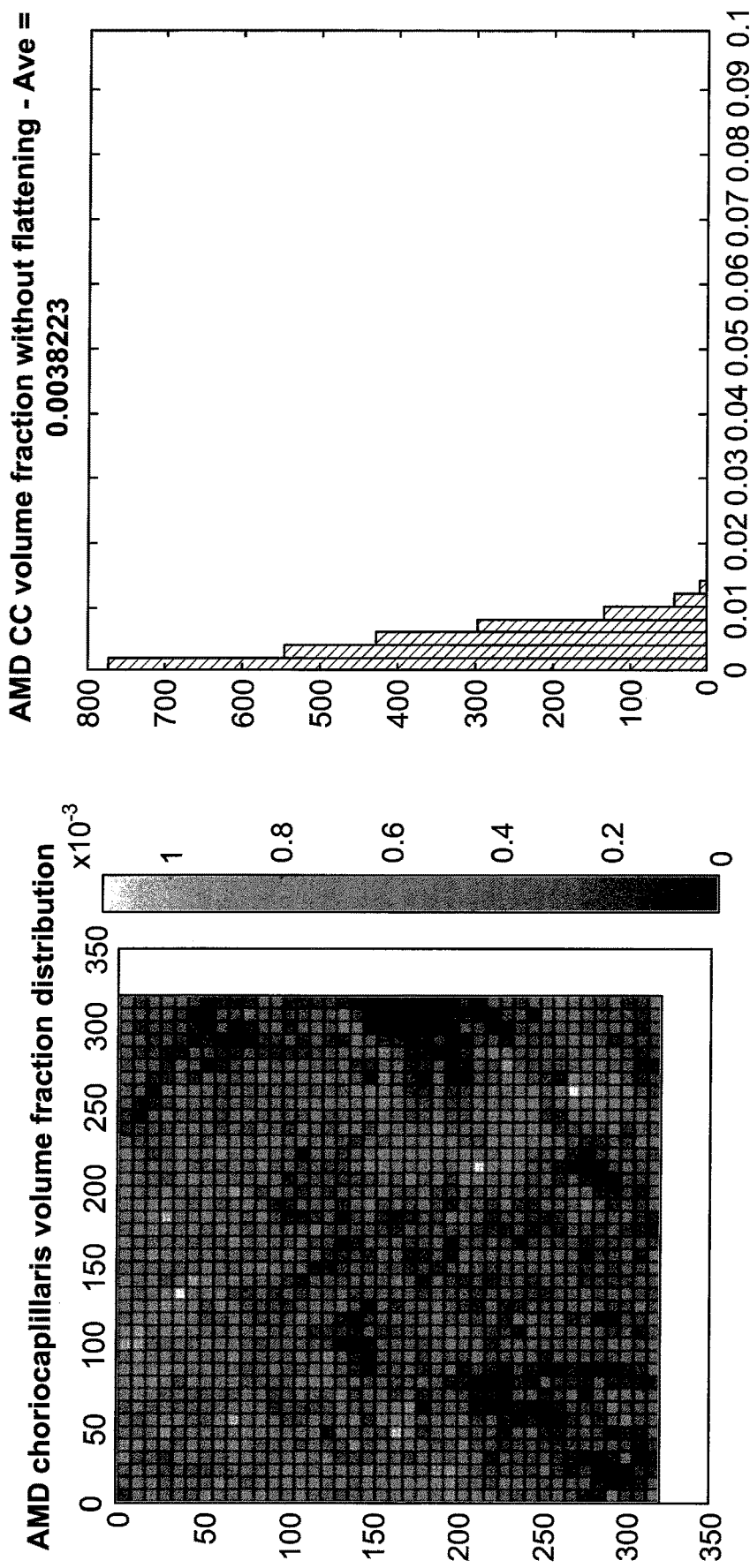
FIG. 24 illustrates a retinal perfusion map and an anisotropy map of retinal perfusion for a diseased eye.

$VR = \lambda_1\lambda_2\lambda_3 / \langle \lambda \rangle^3$ where $\langle \lambda \rangle = (\lambda_1+\lambda_2+\lambda_3)/3$ The resulting FA (and/or RA, VR) anisotropy maps of retinal perfusion can be used for diagnosis. Anisotropy maps of retinal perfusion together with their distribution histograms are shown for a healthy eye and for an eye with AMD in FIGS. 23 and 24 respectively.

A neural network (NN) may be trained with anisotropy maps of retinal perfusion in order to diagnose diseases of the eye (including AMD). This may be implemented using the processing system of FIG. 3 where a number of anisotropy maps are inputted, and the system trained to correctly diagnose those with AMD. The output of the system is a diagnostic parameter representing the stage of the disease or a prognostic tool predicting the likelihood of AMD.

The anisotropy maps may be integrated into the above described ocular model as a "side menu" or additional information feature. The anisotropy maps may also be stand-alone data Use of Neural Networks for Diagnosis, Treatment Planning and Prognosis Deep Learning:

Implementation of image-based deep learning algorithms or neural networks such as convolutional neural networks (CNN), recurrent neural networks (RNN) or long short-term memory (LSTM) networks with one or more of the above derived data relating to an eye can be used to diagnose AMD and other diseases of the eye. Deep learning is a set of learning methods attempting to model data with complex architectures combining different non-linear transformations. For some types of data, especially for images, the data are transformed into vectors, losing the spatial information contained in the images, such as forms. Convolutional neural networks may be preferred for image processing having removed the manual extraction of features. A convolutional neural network acts directly on matrices, or even on tensors for images with three colour channels. A convolutional neural network is composed of several kinds of layers, including: convolutional layers, pooling layers and fully connected layers.

The discrete convolution between two functions f and g is defined as $$(f*g)(x) = \sum_i f(i)g(x+i).$$

For 2-dimensional signals such as images, we consider the 2D-convolutions:

$$(K*I)(i, j) = \sum_{m,n} K(m, n)I(i+n, j+m).$$

At each position, the method generates the convolution between the kernel and the part of the image that is currently treated. Then, the kernel moves by a number s of pixels, where s is called the stride. A small stride results in redundant information. Zero padding can be added, which is a margin of size p containing zero values around the image in order to control the size of the output. The method applies $C_O$ kernels (also called filters), each of size k×k on an image. If the size of the input image is $W_i \times H_i \times C_i$ (Wi denotes the width, Hi the height, and $C_i$ the number of channels, typically $C_i$=3), the volume of the output is $W_O \times H_O \times C_O$, where $C_O$ corresponds to the number of kernels that we consider, and $$W_0 = \frac{W_i - k + 2p}{s} + 1$$
$$H_0 = \frac{H_i - k + 2p}{s} + 1.$$

If the image has 3 channels and if $K_l$ (l=1, ..., $C_O$) denote 5×5×3 kernels (where 3 corresponds to the number of channels of the input image), the convolution with the image I with the kernel $K_l$ corresponds to the formula:

$$K_l * I(i, j) = \sum_{c=0}^{2}\sum_{n=0}^{4}\sum_{m=0}^{4} K_l(n, m, c) I(i+n-2, i+m-2, c).$$

More generally, for images with C i channels, the shape of the kernel is (k, k, $C^i$, $C^O$) where $C^O$ is the number of output channels (number of kernels) that we consider.

The number of parameter associated with a kernel of shape (k, k, $C^i$, $C^O$) is (k×k×$C^i$+1)×$C^O$ The convolution operations are combined with an activation function φ (generally the Relu activation function): if we consider a kernel K of size k×k, if x is a k×k patch of the image, the activation is obtained by sliding the k×k window and computing $z(x) = \phi(K*x+b)$, where b is a bias.

Diagnosis using Convolutional Neural Networks (CNN):

In one embodiment, a convolutional neural network (CNN) is trained using anatomical, physiological and/or functional data relating to an eye in order to diagnose one or more diseases. The steps of this method are described in more detail below with reference to FIGS. 25 and 28 and may be implemented using the processing system 220 of FIG. 3.

Figure 28:
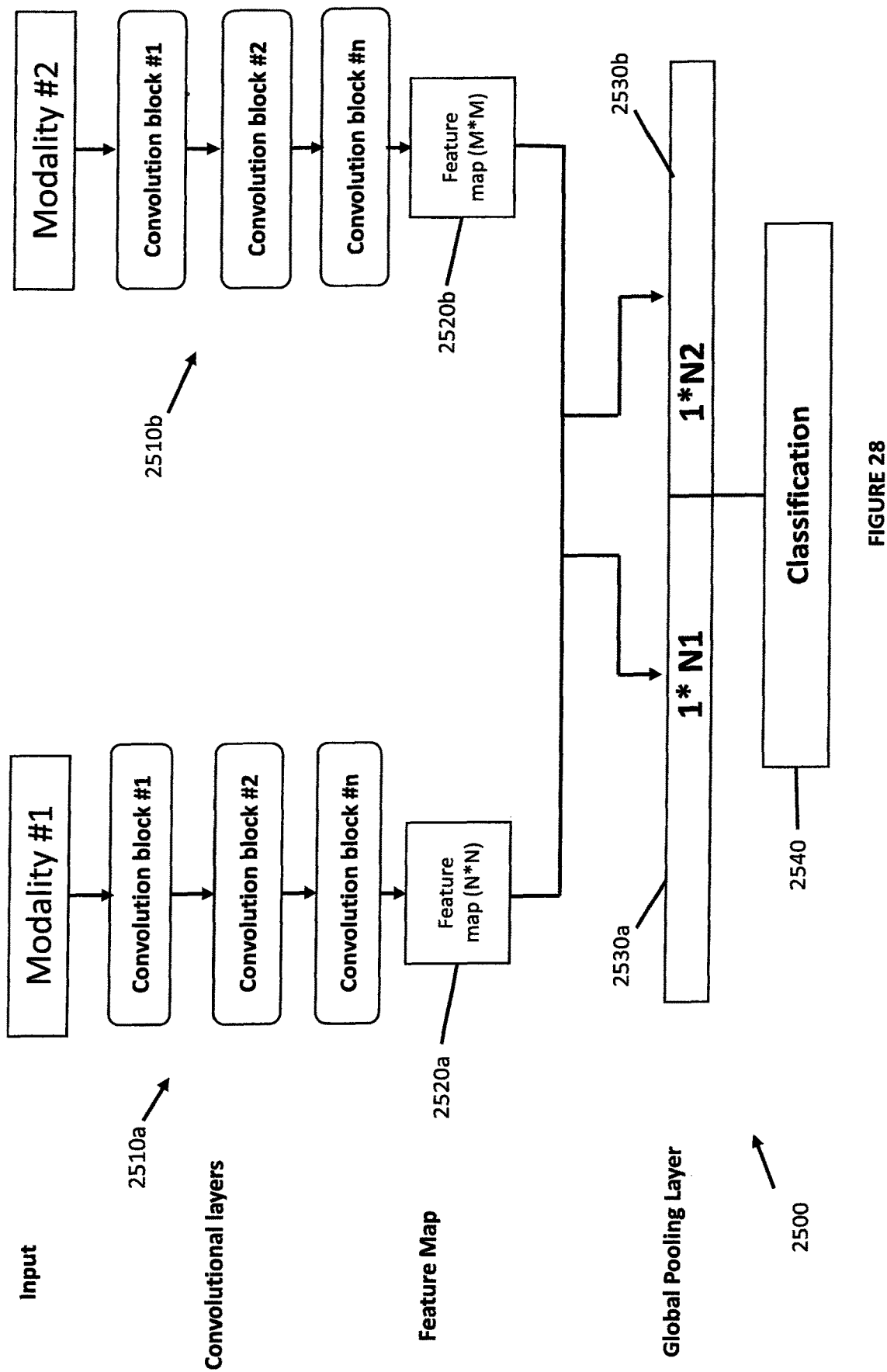
FIG. 28 is a flow chart of a method of diagnosing eye diseases using artificial neural networks according to one embodiment of the invention.

There is provided one or more neural networks, each configured to analyse eye image data. In the exemplary embodiments of FIGS. 25 and 28 there is an ensemble neural network 2500 which comprises a plurality of component or sub-neural networks 2510a, 2510b, etc. Each of the neural networks is configured to analyse eye image data from preferably a different modality, although two different sets of data from the same modality may also be used. As shown in FIG. 28, each neural network 2510 may comprise a plurality of convolution blocks, each containing a plurality of layers, as is known in the art.

Figure 25:
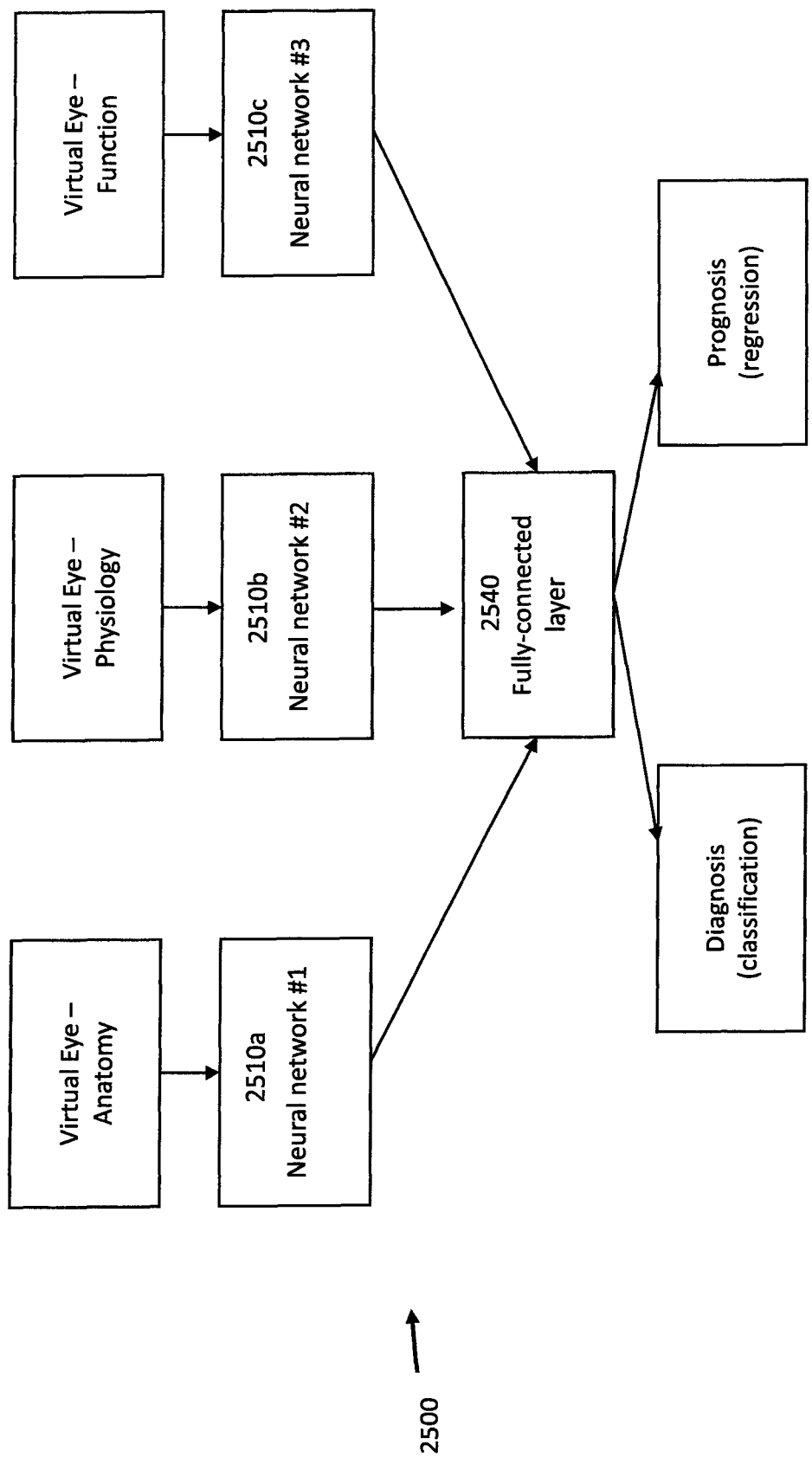
FIG. 25 is a flow chart of a method of diagnosing eye diseases using artificial neural networks according to one embodiment of the invention.

In the example of FIG. 25, three parallel CNNs 2510 are used, each trained separately on different data types, for example different imaging modalities and/or anatomical, physiological or functional data relating to the eye (FIG. 25). Alternatively, the ensemble neural network 2500 may be trained using data from the different imaging modalities.

In the example of FIG. 25, each CNN 2510 generates an output probability of the likelihood of a diagnosis for example the presence of AMD. A logical fully-connected layer takes inputs from each CNN and uses them to generate a diagnosis. The final diagnosis will be made through a "Support Vector Machine" or "random forest" algorithm. In the example of FIG. 28, the output of each CNN 2510 is a feature map 2520, for example in the form of an N*N matrix, highlighting attributes the neural network has learned from a particular input. Each of the feature maps from the CNNs 2510 is used to generate a one dimensional array 1*N1 etc 2530 for each of the CNNs 2510, for example in a global pooling layer. The global pooling layer may generate the one dimensional arrays 2530 through a combination of resorting, moving averages and normalisation, for example.

The ensemble neural network 2500 of FIG. 28 further comprises a fully connected layer 2540, labelled "classification" in FIG. 28. The fully connected layer 2540 combines the outputs from each of the neural networks 2510 and generates a diagnostic parameter for the eye. For example, in one embodiment, the fully connected layer may average the probability outputs from each of the neural networks 2510 and, if above a predetermined threshold, indicates an AMD or other disease diagnosis. In other embodiments, the fully connected layer 2540 may concatenate and weight the outputs from each of the neural networks 2510, for example the one dimensional arrays 2530, to generate the diagnostic parameter. The manner in which the outputs from each of the neural networks 2510 is weighted may be determined on a case-by-case basis dependent on the nature of the data, the structure of the neural networks, the degree of importance placed on the data from each modality, and other factors.

CNN training is known and includes presenting the CNN (s) with many data known sets and "correcting" its output until this is within a suitable tolerance of a correct diagnosis. Various training algorithms may be used to automatically set the internal weightings of the CNN, additionally supervised training may also be performed where some weights are set manually to improve diagnostic accuracy. CNN training is therefore not further described here.

Once the ensemble CNN 2500 has been suitably trained, new anatomical, physiological and/or functional data sets may be input in order to generate a diagnosis, for example in the form of a diagnostic parameter providing an indication of the diagnosis. The diagnosis can be in the form of 'classification' CNN to determine the existence of a pathology, or alternatively in 'regression' CNN mode to determine the likelihood and/or severity of the disease. The classification and regression CNN may each be appropriately trained. The classification output may be in the form of "Yes" or "No" in respect of the eye having a particular disease such as AMD. The regression output may be in the form of a number in a predetermined scale to indicate the severity of the disease, for example 5 out of 10. Alternatively the diagnostic parameter may be in the form of a probability that a particular disease exists in the eye. The diagnostic parameter may also comprise an indication of the uncertainty, or level of confidence in the probability or other output.

The anatomical data input into the ensemble neural network 2500 may be a data set combining data representative of the eye in different modalities, for example in the form of a model of the eye derived from any of the methods previously described either performed independently or derived from the ocular model.

The physiological data may be one or more anisotropic maps, for example anisotropy maps of retinal profusion as described previously, or any other physiological data described herein or otherwise. The anatomical and functional data which could be used may be any such data as described herein, for example the anatomical data may be derived from an image processing system such as fundus photography, magnetic resonance imaging (MRI), X-ray, computer tomography (CT), optical coherence tomography (OCT). The anatomical data may be derived from the ocular model of the first aspect, or directly from the first and second processed image data of the first aspect. Additional or alternative anatomical, physiological and/or functional data may also be used.

Tests of the application of the above-described method have indicated marked improvements in the accuracy, sensitivity and specificity of the diagnosis of eye conditions using ensemble neural networks based on two modalities, and even more marked improvements based on three modalities, when compared to a neural network based on only a single modality or when analyses using neural networks based on single modalities are considered together. That is, the interaction of analyses between the modalities in the ensemble neural network achieves marked improvements in performance.

By way of example, Table 1 below shows improvements in sensitivity in detecting AMD in patients using ensemble CNNs analysing different numbers and types of modalities. It can be seen that, in the test data in this case, 100% sensitivity was found when CNN was based on two or more modalities:

TABLE 1

Sensitivity of different CNN designs in classifying AMD

| Modality | Sensitivity Detecting AMD |
|---|---|
| Single: OCT | 77.8% |
| Single: OCT-A | 97.6% |
| Single: Colour fundus photograph (CFP) | 100% |
| Dual: OCT + OCT-A | 100% |
| Dual: OCT + CFP | 100% |
| Triple: OCT + OCT-A + CFP | 100% |

The specificity in detecting AMD was also the highest for the three modality CNN structure in the same data. A similar trend of an improvement in sensitivity, specificity and accuracy was also identified in identifying young and old patients from the data, therefore showing the ability of embodiments of the technology to recognise aging.

To understand the different sensitivities to each modality, 'attention maps' of each modality were generated to illustrate the image features that were 'noticed' by the neural networks for each modality. A very specific example is that, when using optical coherence tomography (OCT) data, the en-face OCT images revealed that the highest attention was directed to the background homogeneity with a lesser emphasis on the fovea. The lack of attention to the fovea is at first review rather surprising, but perhaps can be explained by the fact that very few of the test patients had subfoveal pathology and none had neovascular AMD. It should also be noted that different modalities (and hence their portions of the trained CNN ensemble) are inherently more sensitive to one aspect (physiological, anatomical or functional) of tissue change (e.g. normal aging vs pathology). One example is that OCT was also found to be more sensitive to ageing rather than pathology, which is also curious. Increasing age is associated with progressive changes within Bruch's membrane and it is conjectured that this manifests as subtle variations in the reflectance and/or transmission patterns within the enface OCT image that thus far have gone unrecognised.

Analysis of the attention maps shows that optical coherence tomography angiography (OCT-A), in contrast, appears to be more sensitive to disease. Within the OCT-A images, the regions of higher attention were the retinal vessels and the tissues immediately adjacent to them. Again the fovea appeared to contribute very little to the OCT-A CNN classifier. These findings are unexpected as intuitively one would not expect the retinal vessels to be predictive of AMD.

From other analysis from the same dataset, it was observed that the vascular density of the choriocapillaris was significantly reduced in patients with AMD compared to controls. Therefore one explanation of the above unexpected finding could be that the vascular density of the choriocapillaris in patients with AMD is reduced compared to healthy individuals and as a result the background OCT-A signal is darker compared to healthy controls. If the background signal is darker, then the relative contrast between the projection artefacts and the background signal is greater, and it is this difference that the CNN is paying attention to. Like OCT-A, the colour fundus photographs appear more sensitive to disease rather than ageing but again review of the attention maps revealed that the area that the CNN paid attention to was unexpected. Intuitively one would expect the CNN to pay attention to the central macular, and drusen in particular. Certainly, previous studies that have reported attention maps from single modality CNNs that have used colour photographs suggest that the macular region was important for predicting disease. However, this proves not be the case as the area of highest attention in the current study was the optic disc and the peripapillary region. This finding is unexpected. The three cohorts in the study differed in age but from other reports it is the perivascular region that appears to be an important region factor for the prediction of age. It would therefore appear that the CNN did not simply sorted the three cohorts based on age in this example.

Figure 26:
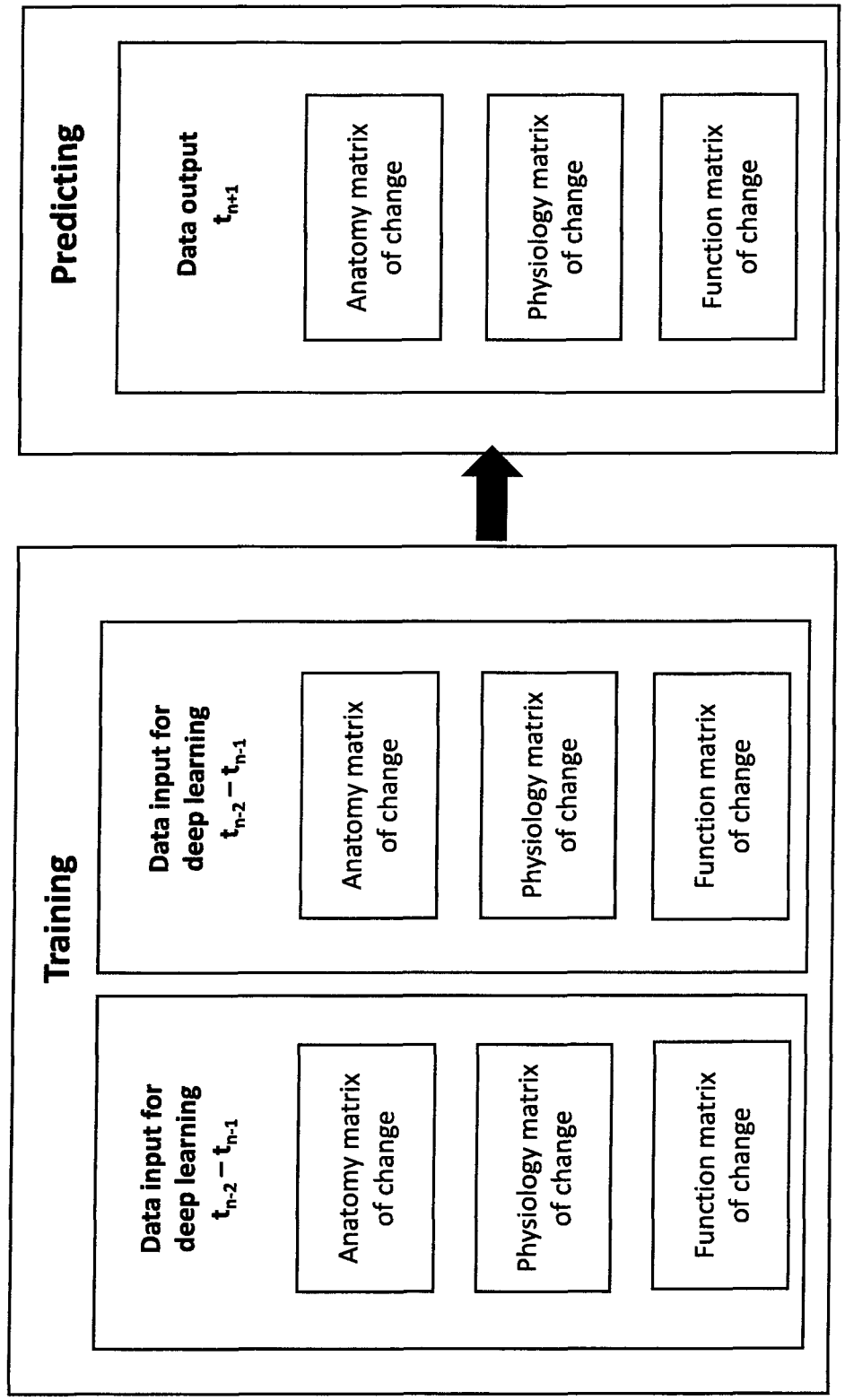
FIG. 26 is a flow chart of a method of generating matrices of change of different data types according to one embodiment of the invention.
Figure 27:
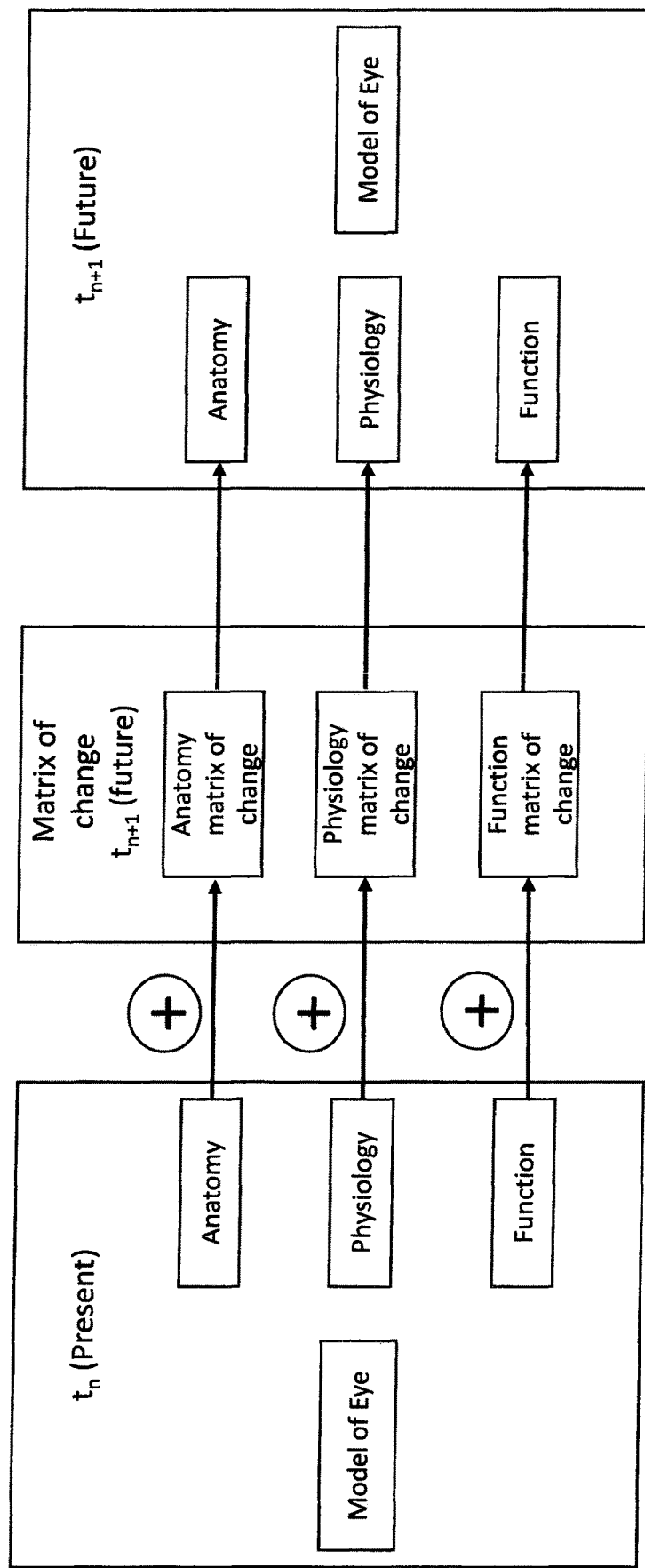
FIG. 27 is a flow chart of a method of prognosing eye diseases using artificial neural networks according to one embodiment of the invention.

Prognosis Using Different Data Types:

Neural network analysis of data representative of the eye, including different types of data (anatomical, physiological, functional) relating to the eye, may also be used for prognosis. The steps of this method are described in more detail below with reference to FIGS. 26, 27 and 29 and may be implemented using the processing system 220 of FIG. 3.

In an embodiment, the method identifies changes in data representative of the eye, for example anatomical, physiological and/or functional data over one or more time intervals in order to generate an eye image change function, for example change matrices, for the data, or each data type. The current data may then be applied to the respective change matrices to generate a prediction of the data in the future. This prediction data may then be used to make a prognosis, indicating the likelihood of disease occurrence within the modelled timeframe.

More particularly, in an embodiment, a neural network is trained using eye image data representative of multiple eyes at two past times $t_{n-1}$ and $t_{n-2}$. By comparing the past eye image data at $t_{n-1}$ and $t_{n-2}$, an eye image change function is generated, which may be in the form of a change matrix or change matrices. Then, the eye image change function is applied to the present eye image data at $t_n$ to generate a prediction for the eye image data at a future time $t_{n+1}$. The prediction data is analysed to generate a prognostic parameter for the eye. For example, the prognostic parameter may be in the form of: "Yes" or "No" in respect of the eye having a particular disease at $t_{n+1}$; a number in a predetermined scale to indicate the severity of the disease at $t_{n+1}$, for example 5 out of 10; or a probability that a particular disease will exist in the eye at $t_{n+1}$. The prognostic parameter may also comprise an indication of the uncertainty, or level of confidence in the probability or other output.

To increase the accuracy of the prognosis, the neural network may be trained using eye image data representative of multiple eyes at further past times. In general, the more data (e.g. the more eyes and the more past times), the greater the accuracy of the prognosis.

In the illustrated embodiments, change functions, or matrices of change, are generated for each of a number of image modalities, for example anatomical, physiological and functional modalities. Examples of such imaging modalities have been described earlier. Past eye image data in each modality is used to generate the change function for each modality in a similar manner to that described above. In embodiments incorporating multiple modalities, the neural network may be an ensemble neural network comprising multiple component or sub-neural networks, each configured to analyse data from one of the modalities, with the ensemble neural network comprising a fully connected layer to receive the outputs from each component neural network and to combine the outputs. The ensemble neural network may further comprise a prediction layer, for example a long short-term memory (LTSM) network to generate a prediction for the eye image data at a future time.

As explained earlier, the fully connected layer may average the probability outputs from each of the neural networks or it may concatenate and weight the outputs from each of the neural networks according to similar factors as described with weighting in the earlier described embodiment.

Figure 29:
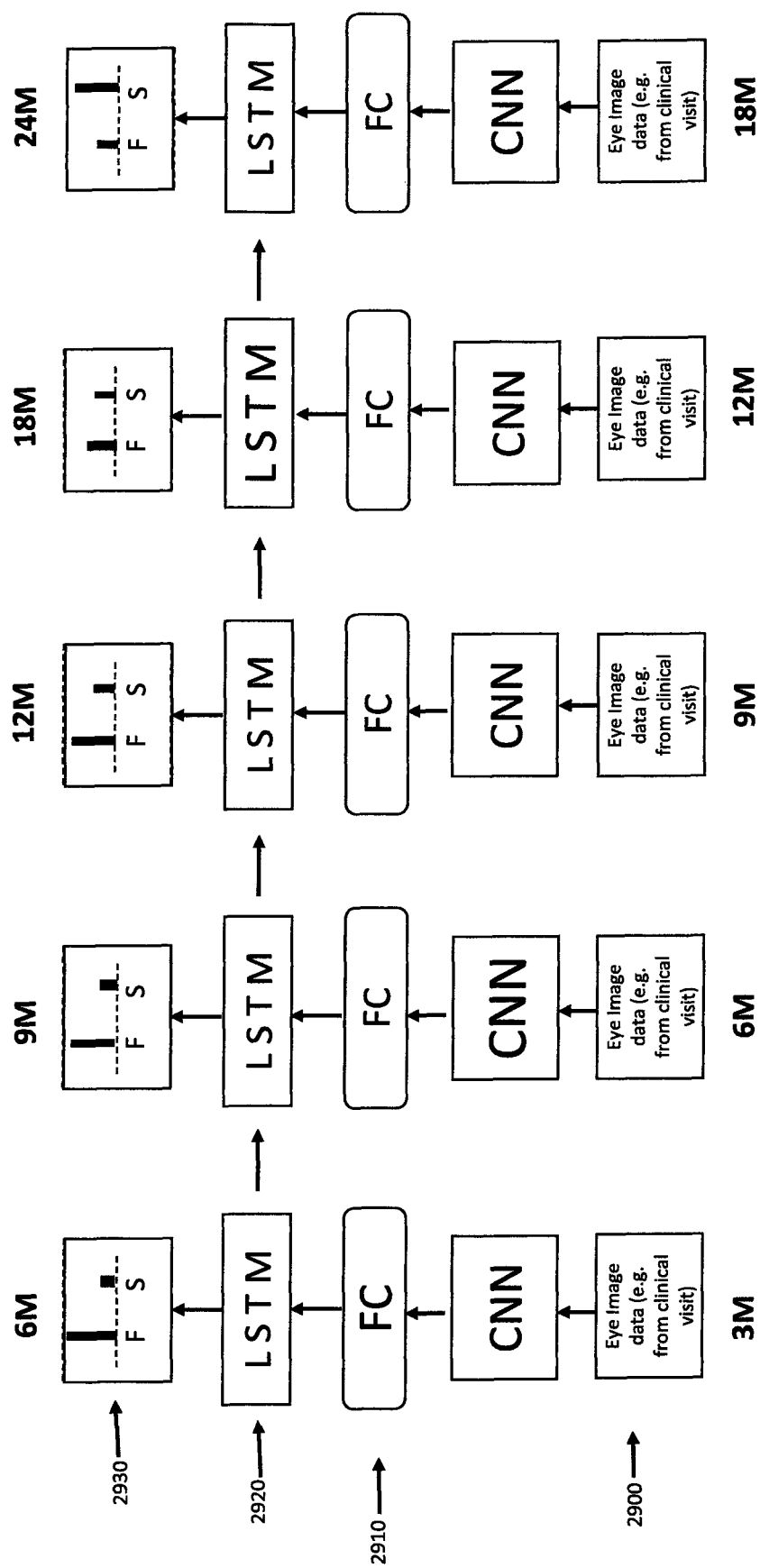
FIG. 29 is a flow chart of a method of prognosing eye diseases using artificial neural networks according to one embodiment of the invention.

In the embodiment of FIG. 29, new eye image data 2900, optionally in multiple modalities, for example in the form of a new ocular model such as the ocular models described earlier in this specification, is created for each clinical visit by the patient to create a "baseline" time-series. This baseline captures the functional, anatomical and/or physiological eye data 2900 of the patient at each point of time. FIG. 29 shows the eye data 2900 as being captured at three monthly intervals (except for the last interval) although this is illustrative only and any time gap may be used. By combining at least two different data sets and/or modalities at each visit, the risk of misdiagnosis due to imaging artefacts is greatly reduced—it is more likely to experience image artefacts in a single image data. Next, areas of change between each of two-time points are extracted by comparing consecutive ocular models (i.e. past and present). The functional, anatomical and physiological data points that are changed within each time interval ($t_{n-1}$–$t_n$) are combined to create matrices of change (functional, anatomical and physiological) for that period. This is achieved using a neural network structured to comprise a convolutional neural network layer 2910, a fully connected layer 2920 to connect multiple neural networks if present, and a long short-term memory (LTSM) network 2930 to predict future eye image data. The upper part of FIG. 29 indicates the increasing accuracy of the analysis over time (F=false, S=success) as more eye image data for the eye is accumulated and available for use in the analysis.

A more detailed description of the generation and use of matrices of change can be found in Jiang, Jiewei, et al. "Predicting the progression of ophthalmic disease based on slit-lamp images using a deep temporal sequence network." PloS one 13.7 (2018): e0201142, and Rivail, Antoine, et al. "Unsupervised Representation Learning of Dynamic Retinal Image Changes by Predicting the Follow-up Image." (2018). The contents of these documents are incorporated by reference herein in their entirety.

It has been described that historical data is used to train the neural network used in the prognosis method. Accurate results may be best obtained using a range of historical eye image data to train the neutral network, including patients with different characteristics, different conditions and different treatment histories, including those patients who have not undergone treatment. Furthermore, past eye treatment data, for example the fact of undergoing treatment or not (e.g. a binary indication), and optionally characteristics of the treatment (e.g. the type of treatment, the intensity of treatment, the time of treatment, etc) may be incorporated into the training data. Therefore, if any of the patients whose data is used in training the neural network experience improvements or other changes in their condition as a result of receiving treatment then this is included within the training data and therefore factored into the analysis process.

As a result of this kind of training, the prediction generated by the neural network may be a treatment prediction parameter as to the condition of the eye in the event treatment occurs, i.e. a 'response to treatment' predictor. That is, the prognostic parameter generated by the neural network, in certain embodiments of the invention, may be made on the assumption of, or conditional on, a specified treatment or treatment parameter, for example the type of treatment, the intensity of treatment, the time of treatment, etc.

Whilst the embodiment has been described with reference to the ocular model, the method may also be used with anatomical, physiological and/or functional data obtained in other ways.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

What is claimed is:

1. A computer-implemented method for prognosing disease in an eye, the method comprising:
   receiving first present eye image data representative of the eye at a present time, the first present eye image data being obtained from a first imaging modality;
   receiving second present eye image data representative of the eye at the present time, the second present eye image data being obtained from a second imaging modality, wherein the second imaging modality is different from the first imaging modality;
   analyzing the first and second present eye image data using a neural network to generate a prediction for future eye image data representative of the eye at a future time; and
   generating a prognostic parameter for the eye from the future eye image data,
   wherein the neural network is trained, using first past eye image data representative of a plurality of eyes at first and second past times in the first imaging modality and using second past eye image data representative of the plurality of eyes at first and second past times in the second imaging modality, to generate one or more eye image data change functions, wherein the eye image data change function is applied by the neural network to the first and second present eye image data to generate the prediction for the future eye image data.

2. The computer-implemented method as claimed in claim 1, wherein the neural network is further trained using first and second past eye image data representative of a plurality of eyes at a third past time in the first and second imaging modalities respectively to refine the eye image data change function.

3. The computer-implemented method as claimed in claim 1, wherein the first and second imaging modalities indicate features of the eye that are selected from the group consisting of: anatomical; physiological; and functional features.

4. The computer-implemented method as claimed in claim 1, wherein the first and second imaging modalities are selected from the group consisting of: magnetic resonance imaging (MRI); fundus photography; optical coherence tomography (OCT); optical coherence tomography angiography (OCTA); X-ray; computer tomography (CT); biometry; ultrasound; keratometry; corneal topography imaging; retinal perfusion mapping and laser speckle flowmetry.

5. The computer-implemented method as claimed in claim 3, wherein the first and second imaging modalities indicate features of the eye that are selected from different members of the group consisting of: anatomical; physiological; and functional features.

6. The computer-implemented method as claimed in claim 1, wherein the eye image data change function comprises one or more matrices of change.

7. The computer-implemented method as claimed in claim 1, wherein the neural network comprises a long short-term memory (LTSM) network.

8. The computer-implemented method as claimed in claim 7, wherein the neural network is an ensemble neural network comprising a first neural network to analyze past and/or present eye image data from the first imaging modality and a second neural network to analyze past and/or present eye image data from the second imaging modality, wherein the ensemble neural network comprises a fully connected layer receiving outputs from each of the first and second neural networks, the output of the fully connected layer being input to the long short-term memory (LTSM) network.

9. The computer-implemented method as claimed claim 1, wherein the method comprises receiving the first past and/or present eye image data and the second past and/or present eye image data as a combined data set.

10. The computer-implemented method as claimed in claim 9, wherein the method comprises receiving the first past and/or present eye image data and the second past and/or present eye image data in the form of data representative of a model of the eye.

11. The computer-implemented method as claimed in claim 10, wherein the data representative of the model of the eye is generated using a method comprising:
   processing the first eye image data to generate first processed eye image data, wherein the first processed eye image data has identified therein one or more features of the eye;
   processing the second eye image data to generate second processed eye image data, wherein the second processed eye image data has identified therein one or more features of the eye;
   registering the first processed eye image data and the second processed eye image data; and
   combining the registered first and second processed eye image data to generate data representative of a model of the eye.

12. The computer-implemented method as claimed in claim 1, wherein the neural network is trained using past eye treatment data representative of prior treatments undergone by the plurality of eyes, and the method comprises generating a treatment prediction parameter comprising the prognostic parameter for the eye on the assumption a treatment is used on the eye.

13. The computer-implemented method as claimed in claim 1, wherein the method further comprises outputting the prognostic parameter for the eye.

* * * * *